(12) United States Patent
Zasloff

(10) Patent No.: US 11,440,936 B2
(45) Date of Patent: Sep. 13, 2022

(54) METHODS AND COMPOSITIONS FOR STIMULATION OF THE INTESTINAL ENTEROENDOCRINE SYSTEM FOR TREATING DISEASES OR CONDITIONS RELATED TO THE SAME

(71) Applicant: Enterin, Inc., Philadelphia, PA (US)

(72) Inventor: Michael Zasloff, Merion, PA (US)

(73) Assignee: Enterin, Inc., Philadelphia, PA (US)

( * ) Notice: Subject to any disclaimer, the term of this patent is extended or adjusted under 35 U.S.C. 154(b) by 0 days.

(21) Appl. No.: 16/039,294

(22) Filed: Jul. 18, 2018

(65) Prior Publication Data

US 2018/0327445 A1 Nov. 15, 2018

Related U.S. Application Data

(63) Continuation of application No. 14/329,627, filed on Jul. 11, 2014, now Pat. No. 10,040,817.

(60) Provisional application No. 61/886,512, filed on Oct. 3, 2013, provisional application No. 62/015,657, filed on Jun. 23, 2014.

(51) Int. Cl.
| | |
|---|---|
| A61K 31/575 | (2006.01) |
| A61P 25/28 | (2006.01) |
| C07J 41/00 | (2006.01) |
| A61P 1/10 | (2006.01) |
| A61K 45/06 | (2006.01) |
| A61P 25/24 | (2006.01) |

(52) U.S. Cl.
CPC ......... *C07J 41/0005* (2013.01); *A61K 31/575* (2013.01); *A61K 45/06* (2013.01); *A61P 1/10* (2018.01); *A61P 25/24* (2018.01); *A61P 25/28* (2018.01)

(58) Field of Classification Search
CPC ... A61K 31/575; A61K 45/06; C07J 41/0005; A61P 25/28
USPC ...................................................... 514/182
See application file for complete search history.

(56) References Cited

U.S. PATENT DOCUMENTS

| | | |
|---|---|---|
| 5,192,756 A | 3/1993 | Zasloff et al. |
| 5,352,682 A | 10/1994 | Sipos |
| 5,637,691 A | 6/1997 | Frye et al. |
| 5,721,226 A | 2/1998 | Frye et al. |
| 5,733,899 A | 3/1998 | Frye et al. |
| 5,763,430 A | 6/1998 | Zasloff |
| 5,792,635 A | 8/1998 | Zasloff |
| 5,795,885 A | 8/1998 | Zasloff et al. |
| 5,834,453 A | 11/1998 | Regen |
| 5,840,740 A | 11/1998 | Zasloff et al. |
| 5,840,936 A | 11/1998 | Zasloff et al. |
| 5,847,172 A | 12/1998 | Zasloff et al. |
| 5,856,535 A | 1/1999 | Zasloff et al. |
| 5,874,597 A | 2/1999 | Jones |
| 5,994,336 A | 11/1999 | Zasloff et al. |
| 6,017,906 A | 1/2000 | Mintz et al. |
| 6,143,738 A | 11/2000 | Zasloff |
| 6,147,060 A | 11/2000 | Zasloff et al. |
| 6,288,089 B1 | 9/2001 | Zawada et al. |
| 6,388,108 B1 | 5/2002 | Rao et al. |
| 6,596,712 B2 | 7/2003 | Zasloff et al. |
| 6,962,909 B2 | 11/2005 | Zasloff et al. |
| 8,247,435 B2 | 8/2012 | Thornthwalte |
| 9,365,608 B2 | 6/2016 | McLane et al. |
| 2004/0198753 A1 | 10/2004 | Kase et al. |
| 2005/0261508 A1 | 11/2005 | Zasloff et al. |
| 2006/0018839 A1* | 1/2006 | Ieni ...................... A61K 9/0043 424/45 |
| 2006/0166858 A1 | 7/2006 | Cundy et al. |
| 2006/0166950 A1 | 7/2006 | Zasloff et al. |
| 2006/0183928 A1 | 8/2006 | Zasloff et al. |
| 2007/0010504 A1 | 1/2007 | Chellquist et al. |
| 2008/0221075 A1 | 9/2008 | Zasloff et al. |
| 2011/0097303 A1 | 4/2011 | Zasloff |
| 2011/0123624 A1 | 5/2011 | Zasloff |

FOREIGN PATENT DOCUMENTS

| | | |
|---|---|---|
| CN | 102813659 | * 12/2012 |
| EP | 0 832 094 B1 | 2/2004 |
| WO | WO 96/08270 A2 | 3/1996 |
| WO | WO 96/40151 | 12/1996 |
| WO | WO 96/40728 A2 | 12/1996 |
| WO | WO 97/44044 A1 | 11/1997 |
| WO | WO 98/19682 A1 | 5/1998 |
| WO | WO 02/28411 A1 | 4/2002 |
| WO | WO 2009/032321 A2 | 3/2009 |
| WO | WO 2011/056650 A2 | 5/2011 |
| WO | WO 2013/158970 A2 | 10/2013 |
| WO | WO 2014/100679 A1 | 6/2014 |

OTHER PUBLICATIONS

Office Action issued in co-pending U.S. Appl. No. 16/035,537, dated Jul. 29, 2019. Notice of Reasons for Rejection issued in co-pending Japanese Patent Application No. 2016-574402, dated Jan. 22, 2019.
Kunze, et al., "Squalamine Reverses Age and Loperamide Associated Dysmotility in a Mouse Biomarker Model of Constipation," *Gastroenterology*, vol. 146, No. 5, page s-356, (May 2014).
Office Action issued in co-pending Chinese Patent Application No. 2015800333337, dated Dec. 3, 2018.
Notice of Allowance issued in co-pending U.S. Appl. No. 15/604,489, dated Oct. 11, 2018.
Notice of Allowance issued in co-pending U.S. Appl. No. 15/604,452, dated Sep. 25, 2018.
Notice of Allowance issued in co-pending U.S. Appl. No. 15/604,527, dated Oct. 16, 2018.
Ahima et al., "Appetite suppression and weight reduction by a centrally active aminosterol." *Diabetes*, 51(7): 2099-104 (2002).
Akhter et al., "Squalamine, a novel cationic steroid, specifically inhibits the brush-border Na+/H+ exchanger isoform NHE3." *Am. J. Physiol.*, 276(1 Pt 1): C136-44 (1999).

(Continued)

*Primary Examiner* — Barbara P Badio
(74) *Attorney, Agent, or Firm* — Foley & Lardner LLP

(57) ABSTRACT

This invention relates to methods of stimulating the activity of the human and animal enteric nervous system. The method comprises orally administering an aminoserol, such as squalamine, a naturally occurring aminosterol isolated from *Squalus acanthias*, or derivatives thereof, to a subject in need.

11 Claims, 6 Drawing Sheets

(56) References Cited

OTHER PUBLICATIONS

Alexander et al., Membrane surface charge dictates the structure and function of the epithelial na+/h+ exchanger. EMBO J., 30:679-691. (2011).
Bhargava et al., "A phase I and pharmacokinetic study of squalamine, a novel antiangiogenic agent, in patients with advanced cancers," Clin. Cancer Res., 7(12): 3912-9 (2001).
Delgado et al., "Neuroprotective effect of vasoactive intestinal peptide (VIP) in a mouse model of Parkinson's disease by blocking microglial activation." Faseb. J., 17(8): 944-6 (2003).
Genaidy et al., "Effect of squalamine on iris neovascularization in monkeys." Retina, 22(6): 772-8 (2002)[ABSTRACT].
Gressens et al., "Vasoactive intestinal peptide prevents excitotoxic cell death in the murine developing brain," J. Clin. Invest., 100(2): 390-7 (1997).
Hao et al., "A Phase I and pharmacokinetic study of squalamine, an aminosterol angiogenesis inhibitor," Clin. Cancer Res., 9(7): 2465-71 (2003).
Herbst et al., "A phase I/IIA trial of continuous five-day infusion of squalamine lactate (MSI-1256F) plus carboplatin and paclitaxel in patients with advanced non-small cell lung cancer," Clin. Cancer Res., 9(11): 4108-15 (2003).
Gonzalez-Rey et al., "Therapeutic effect of vasoactive intestinal peptide on experimental autoimmune encephalomyelitis: down-regulation of inflammatory and autoimmune responses," Am. J. Pathol., 168(4): 1179-88 (2006).
Higgins et al., "Squalamine improves retinal neovascularization," Invest. Ophthalmol. Vis. Sci., 41(6): 1507-12 (2000).
MacDonald, D. (1995). "Squalamine for STDs." Abstract No. F7 35th ICAAC conference, 45 pages.
Moore et al., "Squalamine: an aminosterol antibiotic from the shark," Proc. Natl. Acad. Sci. USA, 90(4): 1354-8 (1993).
Rao et al., "Aminosterols from the dogfish shark Squalus acanthias," J. Nat. Prod., 63(5): 631-5 (2000) [ABSTRACT].
Li et al., "GLP-1 receptor stimulation preserves primary cortical and dopaminergic neurons in cellular and rodent models of stroke and Parkinsonism," Proc. Natl. Acad. Sci. USA, 106(4): 1285-90 (2009).
Li et al., "Squalamine and cisplatin block angiogenesis and growth of human ovarian cancer cells with or without HER-2 gene overexpression," Oncogene, 21(18): 2805-14 (2002).
Higgins et al., "Regression of retinopathy by squalamine in a mouse model," Pediatr. Res., 56(1): 144-9 (2004).
Salmi et al., "New stereoselective titanium reductive amination synthesis of 3-amino and polyaminosterol derivatives possessing antimicrobial activities," Eur. J. Med. Chem., 43(3): 540-7 (2008) [ABSTRACT].
Schiller, J. H. and G. Bittner, "Potentiation of platinum antitumor effects in human lung tumor xenografts by the angiogenesis inhibitor squalamine: effects on tumor neovascularization," Clin. Cancer Res., 5(12): 4287-94 (1999).
Selinsky et al., "Squalamine is not a proton ionophore," Biochim. Biophys. Acta., 1464(1): 135-41 (2000).
Selinsky et al., "The aminosterol antibiotic squalamine permeabilizes large unilamellar phospholipid vesicles," Biochim. Biophys. Acta., 1370(2): 218-34 (1998).
Sills et al., "Squalamine inhibits angiogenesis and solid tumor growth in vivo and perturbs embryonic vasculature," Cancer Res., 58(13): 2784-92 (1998).
Salmi et al., "Squalamine: an appropriate strategy against the emergence of multidrug resistant gramnegative bacteria?" PLoS ONE, 3(7): e2765 (2008).
Sokoloff et al., "Adjunctive therapy for men with high risk localized and locally advanced prostate cancer: targeting disseminated tumor cells," J. Urol., 172(6 Pt 2): 2539-44 (2004) [ABSTRACT].
Tirassa et al., "CCK-8 prevents the development of kindling and regulates the GABA and NPY expression in the hippocampus of pentylenetetrazole (PTZ)-treated adult rats," Neuropharmacology, 48(5): 732-42 (2005) [ABSTRACT].

Sumioka et al., "TARP phosphorylation regulates synaptic AMPA receptors through lipid bilayers," Neuron, 66(5): 755-67 (2009).
Verdin et al., "Characterization of a common high-affinity receptor for reovirus serotypes 1 and 3 on endothelial cells," J. Virol., 63(3): 1318-25 (1989).
White et al., "Therapeutic potential of vasoactive intestinal peptide and its receptors in neurological disorders," CNS Neurol. Disord. Drug Targets, 9(5): 661-6 (2010).
Williams et al., "Squalamine treatment of human tumors in nu/nu mice enhances platinum-based chemotherapies," Clin. Cancer Res., 7(3): 724-33 (2001).
Yeung et al., "Membrane phosphatidylserine regulates surface charge and protein localization," Science, 319(5860): 210-3 (2008) [ABSTRACT].
Zasloff, M., "Antimicrobial peptides of multicellular organisms," Nature, 475(6870): 389-95 (2002) [ABSTRACT].
Yin et al., "Antiangiogenic treatment delays chondrocyte maturation and bone formation during limb skeletogenesis," J. Bone Miner. Res., 17(1): 56-65 (2002).
Zasloff et al., "A spermine-coupled cholesterol metabolite from the shark with potent appetite suppressant and antidiabetic properties," Int. J. Obes. Relat. Metab. Disord., 25(5): 689-97 (2001).
Zasloff et al., "Squalamine as a broad-spectrum systemic antiviral agent with therapeutic potential," Proc. Natl. Acad. Sci. USA, 108(38): 15978-83 (2011).
Steinberg, B. E. and S. Grinstein, "Pathogen destruction versus intracellular survival: the role of lipids as phagosomal fate determinants," J. Clin. Invest., 118(6): 2002-11 (2008).
International Search Report and Written Opinion issued in related International Patent Application No. PCT/US2015/036935, dated Sep. 30, 2015.
Takahashi, et al., "A novel aminosterol reverses diabetes and fatty liver disease in obese mice," Journ. of Hepatology, vol. 41, No. 3, pp. 391-398 (2004).
International Preliminary Report on Patentability issued in related International Patent Application No. PCT/US2015/036935, dated Dec. 27, 2016.
Wolfgang Kunze, et al., "Squalamine Reverses Age and Loperamide Associated Dysmotility in a Mouse Biomarker Model of Constipation," G''stroenterology, vol. 146, No. 5, page S-356 (May 2014).
Communicated issued in related European Patent Application No. 15 811 714.3, dated Jan. 2, 2018.
Search Report issued in related co-pending European Patent Application No. 15 811 714.3, dated Apr. 12, 2018.
Non-Office Action issued in related U.S. Appl. No. 15/604,452, dated May 11, 2018.
Brian E. Lacy et al., "Lubiprostone: chronic constipation and irritable bowel syndrome with constipation," Expert Opinion on Pharmacotherapy, vol. 10, No. 1, pp. 143-152 (Dec. 2008).
Office Action issued in co-pending U.S. Appl. No. 15/604,489, dated Jun. 15, 2018.
Notice of Allowance issued in co-pending U.S. Appl. No. 14/329,627, dated Jun. 27, 2018.
Office Action issued in co-pending U.S. Appl. No. 15/604,527, dated Jul. 3, 2018.
Baird et al., "Age-related macular degeneration and DNA methylation," Epigenomics (2013), 5(3), pp. 239-241.
Ciulla et al., "Squalamine lactate for treatment of age-related macular degeneration," Expert Review of Opthalmology, vol. 2, No. 2, pp. 165-175 ISSN: 1746-9899 (2017).
Office Action issued in co-pending U.S. Appl. No. 16/035,537, dated Jan. 11, 2019.
Office Action issued in co-pending U.S. Appl. No. 16/219,879, dated Feb. 12, 2020.
Office Action issued in co-pending U.S. Appl. No. 16/219,848, dated Apr. 21, 2020.
Notice of Allowance issued in co-pending U.S. Appl. No. 16/219,848, dated Dec. 8, 2020.
Office Action issued in co-pending U.S. Appl. No. 16/219,848, dated Jan. 17, 2020.
Notice of Allowance issued in co-pending U.S. Appl. No. 16/035,557, dated Dec. 23, 2019.

\* cited by examiner

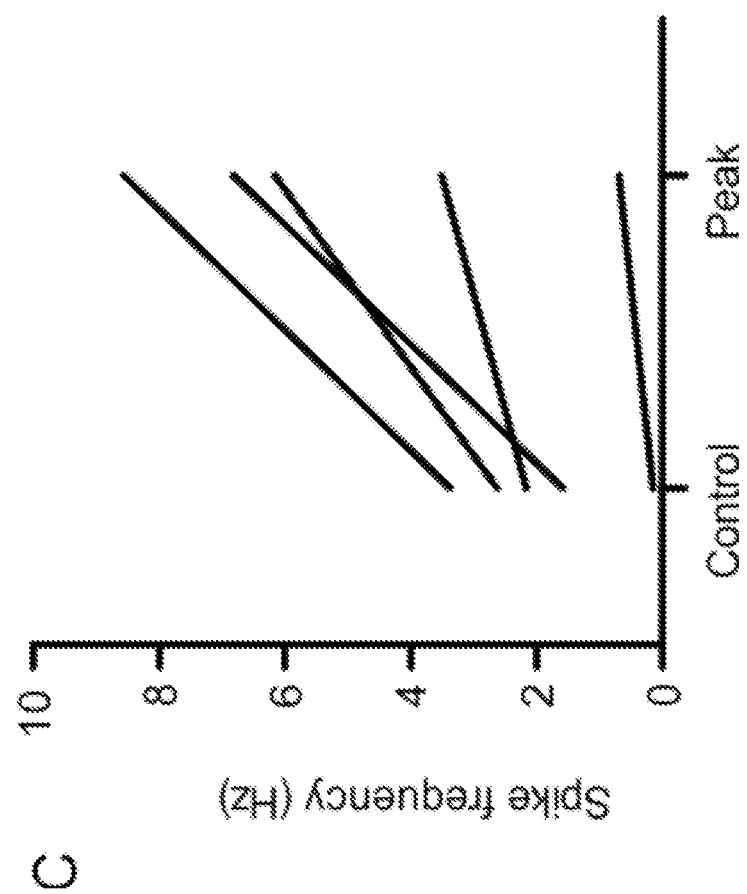

METHODS AND COMPOSITIONS FOR STIMULATION OF THE INTESTINAL ENTEROENDOCRINE SYSTEM FOR TREATING DISEASES OR CONDITIONS RELATED TO THE SAME

CROSS-REFERENCE TO RELATED APPLICATION

This application is a continuation application of U.S. application Ser. No. 14/329,627, filed on Jul. 11, 2014, which claims priority to U.S. Provisional Patent Application No. 62/015,657, filed on Jun. 23, 2014, and U.S. Provisional Patent Application No. 61/886,512, filed on Oct. 3, 2013. The contents of these applications are incorporated herein by reference in their entirety.

FIELD OF THE INVENTION

This invention relates to methods of stimulating the activity of the human and animal enteric nervous system, which is useful in the treatment of various diseases or conditions. The method comprises orally administering to a subject in need squalamine, a naturally occurring aminosterol isolated from *Squalus acanthias*, or derivatives thereof. The method results in the controlled activation of the intestinal enteric nervous system. The method is useful for the treatment of gastro-intestinal motility disorders such as chronic idiopathic constipation, Opioid induced constipation, irritable bowel syndrome and inflammatory bowel disease, diabetes, and neurodegenerative diseases, such as Parkinson's disease, Alzheimer's disease, dementia of aging, Huntington's chorea, neuropathy of diabetes, peripheral sensory neuropathy, traumatic head and/or spine injury, stroke, Amyotrophic lateral sclerosis, multiple sclerosis, depression, epilepsy and autism. In addition, the method is useful for the treatment and prevention of a variety of malignancies, including those of the colon, pancreas, liver, brain, male and female genitourinary tract, lymphatic and blood tissues, lungs, skin, breast, and endometrium.

BACKGROUND OF THE INVENTION

Chemically squalamine presented a structure never before seen in nature, that being a bile acid coupled to a polyamine (spermidine):

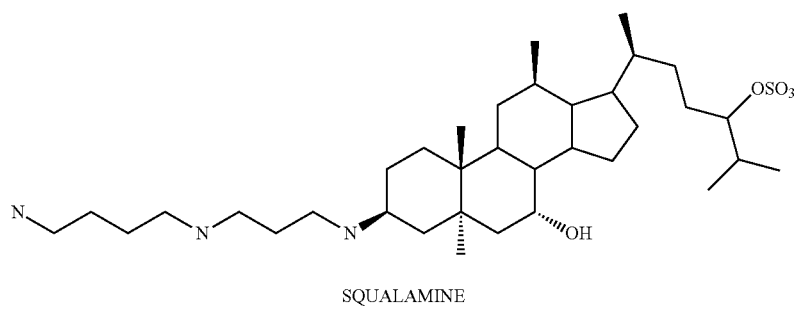

SQUALAMINE

The discovery of squalamine, the structure of which is shown above, was reported by Michael Zasloff in 1993 (U.S. Pat. No. 5,192,756). Squalamine was discovered in various tissues of the dogfish shark (*Squalus acanthias*) in a search for antibacterial agents. The most abundant source of squalamine is in the livers of *Squalus acanthias*, although it is found in other sources, such as lampreys (Yun et al., "Identification of Squalamine in the Plasma Membrane of White Blood Cells in the Sea Lamprey," *Petromyzon marinus*," *J. Lipid Res.*, 48(12): 2579-2586 (2007)).

Numerous studies later demonstrated that squalamine exhibits potent antibacterial activity in vitro (Salmi, Loncle et al. 2008). Subsequently, squalamine was discovered to exhibit antiangiogenic activity in vitro and upon administration to animals (Sills, Williams et al. 1998; Yin, Gentili et al. 2002). As a consequence, squalamine has been evaluated in disease states known to be associated with pathological neovascularization, such as cancer (Sills, Williams et al. 1998; Schiller and Bittner 1999; Bhargava, Marshall et al. 2001; Williams, Weitman et al. 2001; Hao, Hammond et al. 2003; Herbst, Hammond et al. 2003; Sokoloff, Rinker-Schaeffer et al. 2004), and vascular disorders of the eye, including macular degeneration (US2007/10504A1 2007), retinopathy of prematurity (Higgins, Sanders et al. 2000; Higgins, Yan et al. 2004; US2007/10504A1 2007), corneal neovascularization (Genaidy, Kazi et al. 2002) and diabetic retinopathy (US2007/10504A1 2007).

The utility of squalamine as an anti-infective has been demonstrated in vitro against bacteria and fungi (Moore, Wehrli et al. 1993; Rao, Shinnar et al. 2000; Salmi, Loncle et al. 2008). Squalamine is a cationic amphipathic substance exhibiting an affinity for membranes composed of anionic phospholipids (Selinsky, Zhou et al. 1998; Selinsky, Smith et al. 2000). Like other such agents, including magainin and cationic antimicrobial peptides, squalamine is believed to exert antimicrobial action by interacting electrostatically with the membranes of target microorganisms, which generally display anionic phospholipids on the membrane surface exposed to the environment, subsequently disturbing their functional integrity, and causing death of the targeted microbe (Sills, Williams et al. 1998; Zasloff 2002; Salmi, Loncle et al. 2008).

Recent studies have highlighted the efficacy of systemically administered squalamine to prevent or treat viral infections in animals (Zasloff et al., "Squalamine as a broad-spectrum systemic antiviral agent with therapeutic potential," *Proc. Natl. Acad. Sci. USA*, 108(38): 15978-83 (2011); US (2011) Ser. No. 12/913,648).

The mechanism of action. It has been reported that squalamine exerts its effects at the cellular level by displacing proteins bound electrostatically to negatively charged membranes, causing pleiotropic changes in the functional state of the cell (Alexander et al., "Membrane surface charge dictates the structure and function of the epithelial na+/h+ exchanger," EMBO J., 30:679-691(2011); Yeung et al., "Membrane phosphatidylserine regulates surface charge and protein localization," *Science*, 319(5860): 210-3 (2008);

Sumioka et al., "TARP phosphorylation regulates synaptic AMPA receptors through lipid bilayers," Neuron, 66(5): 755-67 (2009); Zasloff et al., "Squalamine as a broad-spectrum systemic antiviral agent with therapeutic potential," Proc. Natl. Acad. Sci. USA, 108(38): 15978-83 (2011)).

Aminosterol 1436 is an aminosterol isolated from the dogfish shark, which is structurally related to squalamine (U.S. Pat. No. 5,840,936; Rao, Shinnar et al. 2000). Aminosterol 1436 exhibits antiviral activity against HIV in tissue culture (U.S. Pat. No. 5,763,430) via a mechanism proposed to involve inhibition of a lymphocyte-specific NHE by 1436, resulting in suppression of cytokine responsiveness, and subsequent depression of the capacity of the lymphocyte to support HIV replication (U.S. Pat. No. 5,763,430). Aminosterol 1436, however, has an additional pharmacological property, not shared with squalamine, namely potent appetite suppression and promotion of dose-dependent weight loss (U.S. Pat. No. 6,143,738; Ahima et al., "Appetite suppression and weight reduction by a centrally active aminosterol." Diabetes, 51(7): 2099-104 (2002); Patel et al., 2002).

Prior clinical studies in humans have focused on the anti-angiogenic properties of squalamine. Squalamine in its intravenous form, squalamine lactate, is in the process of being tested as a treatment for fibrodysplasia ossificans progressiva, a rare disease where connective tissue will ossify when damaged. Genesis, A., "Squalamine trial for the treatment of fibrodysplasia ossificans progressiva initiated", Angiogenesis Weekly, 8:45 (2002). Squalamine is also undergoing trials for treatment of non-small cell lung cancer (stage I/IIA) as well as general phase I pharmacokinetic studies. Herbst et al., "A Phase I/IIA Trial of Continuous Five-Day Infusion of Squalamine Lactate (MSI-1256F) Plus Carboplatin and Paclitaxel in Patients with Advanced Non-Small Cell Lung Cancer 1," Clinical Cancer Research, 9:4108-4115 (2003); Hao et al., "A Phase I and Pharmacokinetic Study of Squalamine, an Aminosterol Angiogenesis Inhibitor", Clin Cancer Res., 9(7): 2465-2471 (2003). In 2005, the Food and Drug Administration granted squalamine Fast Track status for approval for treatment of age-related macular degeneration. CATE: California Assistive Technology Exchange," California Assistive Technology Exchange, cate(dot)ca(dot)gov/index.cfm?a=Resources&p=News&article=176, Retrieved 2009-03-31. In 2011, Ohr Pharmaceuticals initiated clinical trials to evaluate squalamine lactate, administered as an eye drop, for the treatment of wet macular degeneration, based on their assessment that sufficiently high concentrations of squalamine can access the retina, when the substance is placed onto the corneal surface. These studies are ongoing. Genaera Corporation discontinued trials for the use of squalamine in treating cancer in 2007. "PROSTATE CANCER; Genaera Discontinues LOMUCIN in Cystic Fibrosis and Squalamine in Prostate Cancer Studies," Drug Week, pp. 251. 2007-07-20; "Reports describe the most recent news from Genaera Corporation," Biotech Business Week, pp. 1540 (2007-09-17). Squalamine is also marketed under the brand name SQUALAMAX™ as a dietary supplement, though it has not been approved as a drug in this form and thus cannot make therapeutic claims. SQUALAMAX™ is an unfractionated extract of shark liver, containing innumerable uncharacterized substances in addition to squalamine, and squalamine is present in SQUALAMAX™ at less than 0.01% of the total weight of the extract. "Cyber Warning Letter", Center for Drug Evaluation and Research (2002-05-06), www(dot)fda(dot)gov/CDER/warn/cyber/2002/CFSANnuGen.htm; Retrieved 2009-03-31. Moreover, the dietary supplement form of squalamine is not pharmaceutical grade squalamine, as pharmaceutical grade squalamine requires significantly greater manufacturing efforts.

By 2006, over 300 patients had received squalamine in doses ranging from 6-700 mg/m$^2$/day by iv administration, in three Phase I and nine Phase II studies. Hao et al., "A Phase I and pharmacokinetic study of squalamine, an aminosterol angiogenesis inhibitor," Clin. Cancer Res., 9:2465-71 (2003); Herbst et al., "A phase I/IIA trial of continuous five-day infusion of squalamine lactate (MSI-1256F) plus carboplatin and paclitaxel in patients with advanced non-small cell lung cancer," Clin. Cancer Res., 9:4108-15 (2003); Bhargava et al., "A phase I and pharmacokinetic study of squalamine, a novel antiangiogenic agent, in patients with advanced cancers," Clin. Cancer Res., 7:3912-9 (2001); and Connolly et al., "Squalamine lactate for exudative age-related macular degeneration," Ophthalmol. Clin. North Am., 19:381-91 (2006). The studies showed that the compound exhibited an acceptable safety profile and evidence of efficacy in these early trials. In 2006 development of squalamine was halted for economic/strategic reasons by Genaera. In 2011 Ohr Pharmaceuticals initiated studies of the compound administered as an eye drop for the treatment of retinal eye disease, but all studies of this compound against cancer have remained in a dormant stage since.

Of relevance to the invention disclosed herein, squalamine has never been studied as an oral agent in a human, and thus its pharmacology and biological effects in man (and other mammals) are known only after intravenous administration. Extensive studies in animals have shown that neither squalamine nor Aminosterol 1436 can be absorbed to any extent from the gastrointestinal tract, requiring parenteral administration for the various previously conceived applications of these compounds. Aminosterol 1436, although capable of inducing weight loss when administered parenterally to dogs, and rodents exhibited no anorectic activity when administered orally, consistent with its poor bioavailability when delivered orally. Indeed, in a published review on the applications of squalamine as a therapeutic, Genaera scientists state "Although squalamine lactate is well absorbed in rodents by the subcutaneous and intraperitoneal routes, preliminary studies indicate that it is poorly bioavailable orally." (Connolly et al., "Squalamine lactate for exudative age-related macular degeneration," Ophthalmol. Clin. North Am., 19:381-91, (2006)) To date, no published patent application or literature reference has documented or reported a pharmacological effect of orally administered squalamine (or any other related aminosterol) in humans or animals. (U.S. Pat. Nos. 5,192,756; 5,637,691; 5,721,226; 5,733,899; 5,763,430; 5,792,635; 5,795,885; 5,840,740; 5,840,936; 5,847,172; 5,856,535; 5,874,597; 5,994,336; 6,017,906; 6,143,738; 6,147,060; 6,388,108; 6,596,712; U.S. Patent Publication No. 2005/0261508A1 2005; U.S. Pat. No. 6,962,909; U.S. Patent Publication No. 2006/0166950A1 2006; U.S. Patent Publication No. 2006/0183928A1 2006; U.S. Patent Publication No. 2007/10504A1 2007.)

Squalamine and related aminosterols, such as 1436, do not exit the gastrointestinal tract into either the portal or systemic blood stream. This resulted in generally accepted conclusions by those skilled in the art of drug development, as of the year 2014, about 20 years after the reported discovery of squalamine, that squalamine could provide no benefit for systemic conditions, including malignancies, when administered orally.

There remains a need in the art for new method of treating diseases and conditions correlated with stimulation of the activity of the human and animal enteric nervous system. The present invention satisfies this need.

SUMMARY OF THE INVENTION

The present invention is directed to methods of stimulating the gastrointestinal tract to achieve certain medical benefits, as described herein. The method comprises orally administering a pharmaceutical composition comprising one or more aminosterols to a subject in need. An "aminosterol" can be squalamine or a derivative thereof, Aminosterol 1436 or a derivative thereof, or a naturally occurring aminosterol isolated from *Squalus acanthias* or a derivative thereof, collectively referred to as "squalamine" herein." The pharmaceutical composition can comprise one or more pharmaceutically acceptable carriers. The subject can be a mammal, including a human.

The invention is based on the discovery of unexpected and unprecedented activity of orally administered squalamine and related aminosterols (e.g., Aminosterol 1436). The activity relates to stimulating a sequence of events within the human GI tract with therapeutic value. The sequence of events stimulated by an aminosterol such as squalamine or a derivative thereof involves the induction of an intestinal secretory response followed by a period of "small intestinal quieting," and the subsequent passage of a normally formed bowel movement. These events are best explained as a consequence of the stimulation of a heretofore unknown physiological gastrointestinal response, in this invention shown to be controlled or initiated by an effective oral dose of an aminosterol such as squalamine or the related aminosterol, 1436 (Aminosterol-Induced GI Response).

Based on the pharmacology of the response, and the likely known components of the gastrointestinal tract that have been engaged, it is possible to predict uses or applications of the methods of the invention. These uses include: (1) treatment and prevention of disorders of gastrointestinal motility, such as chronic idiopathic constipation, Opioid induced constipation, irritable bowel syndrome, and inflammatory bowel disease; (2) treatment and prevention of conditions such as diabetes mellitus and diabetic neuropathy; (3) treatment and prevention of disorders of the nervous system that could benefit from neuro-protection, such as Parkinson's Disease, Alzheimer's disease, Huntington's Disease, acute traumatic injury to the central nervous system, including the spinal cord, stroke, acute head and/or spine injury, degenerative processes associated with aging, including memory loss ("dementia of aging"), cerebral palsy, epilepsy, peripheral sensory neuropathy, and multiple sclerosis; (4) treatment or prevention of a variety of malignancies, and particularly vascularized malignancies, including but not limited to malignancies of the colon, pancreas, liver, brain, male and female genitourinary tract, lymphatic and blood tissues, lungs, skin, breast, and endometrium (unexpected responses, as described herein, include regression of malignancies); (5) treatment or prevention of depression, and (6) treatment or prevention of autism.

The invention comprises orally administering a therapeutically effective amount of squalamine or a derivative thereof, an isomer or prodrug of squalamine, or a pharmaceutically equivalent salt thereof to a subject, such as a mammal, in need. A "subject in need" is a human or mammal with a disorder in which the stimulation of the "Aminosterol-Induced GI Response" would provide therapeutic or medical benefit.

Preferably, the squalamine is a pharmaceutical grade squalamine. The composition can further comprise one or more pharmaceutically acceptable excipients. The squalamine or derivative thereof is present in an amount sufficient to produce the intended benefit or response.

In another embodiment, the invention encompasses methods of treating and/or preventing conditions benefitted by the stimulation of the Aminosterol-Induced GI Response comprising administering a therapeutically effective amount of an aminosterol that can inhibit the formation of actin stress fibers in endothelial cells stimulated by a ligand known to induce stress fiber formation. An exemplary aminosterol useful in the methods of the invention has the chemical structure of Formula I:

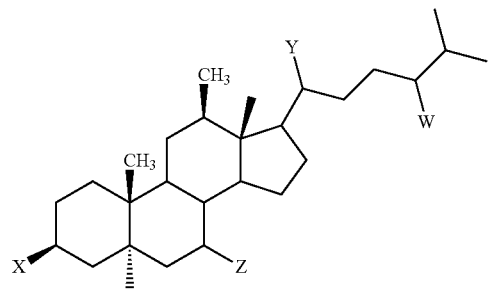

wherein,
W is 24S—$OSO_3$ or 24R—$OSO_3$;
X is 31-$H_2N$—$(CH_2)_4$—NH—$(CH_2)_3$—NH— or 3α-$H_2N$—$(CH_2)_4$—NH—$(CH_2)_3$—NH—;
Y is 20R—$CH_3$; and
Z is 7α or 7β-OH.

In another embodiment of the invention, the aminosterol is one of the naturally occurring aminosterols (1-8) isolated from *Squalus acanthias*:

Compound 1

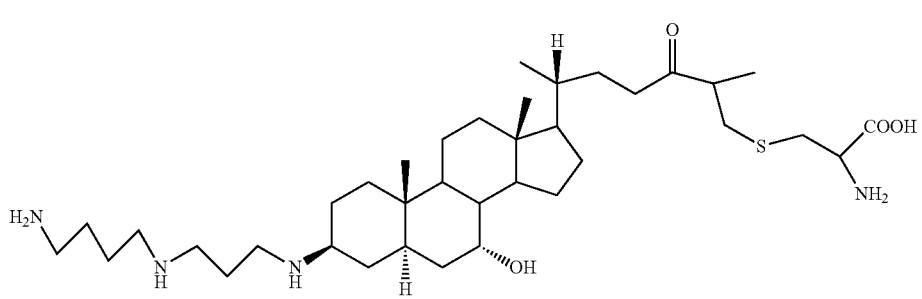

Compound 2
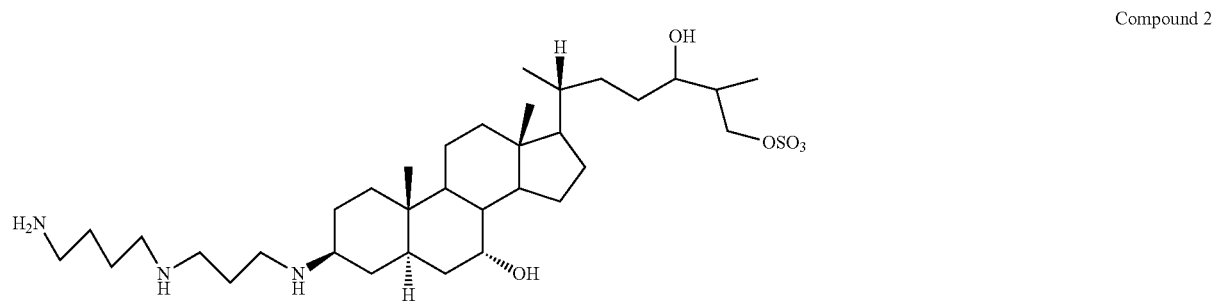
Compound 3
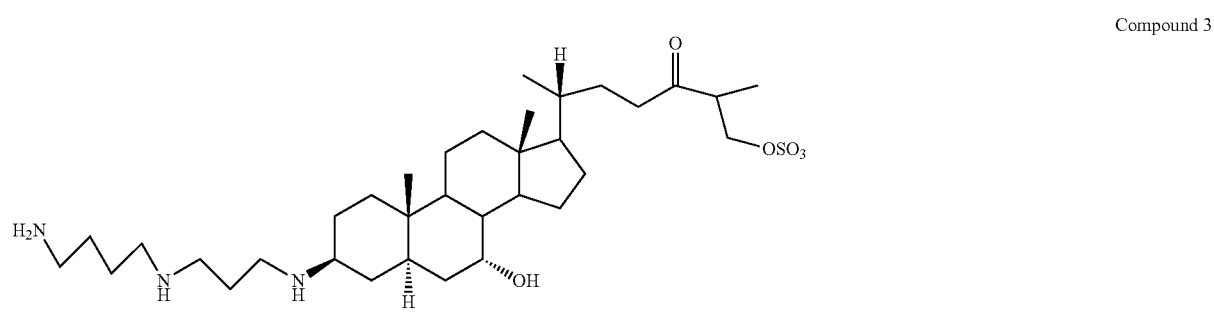
Compound 4                                          Compound 5
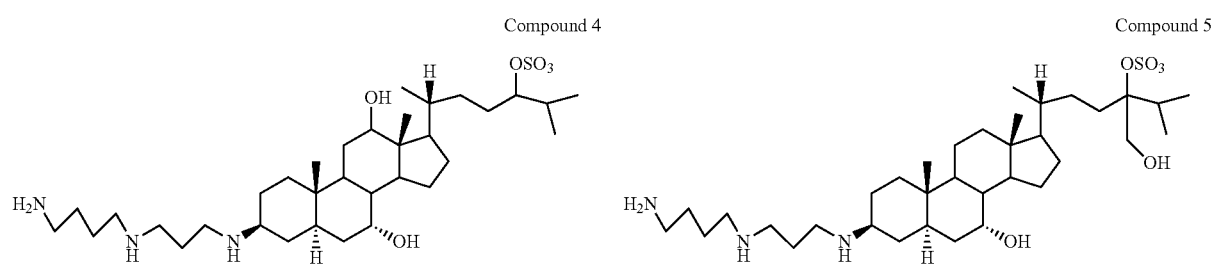
Compound 6
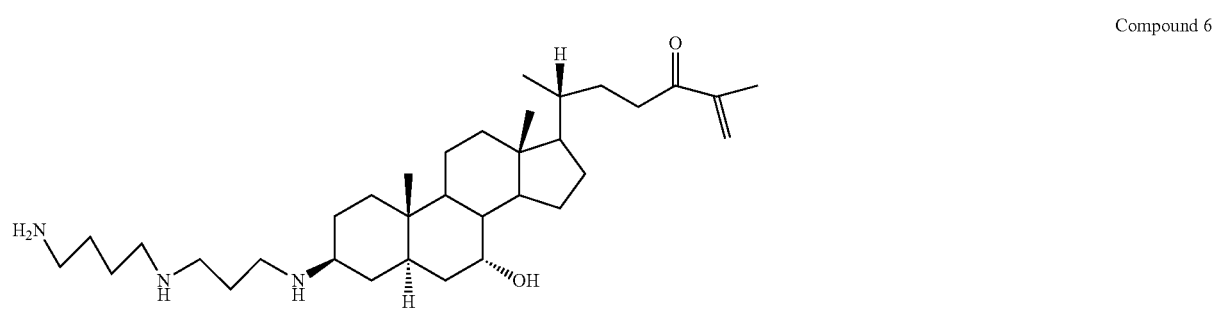
Compound 7
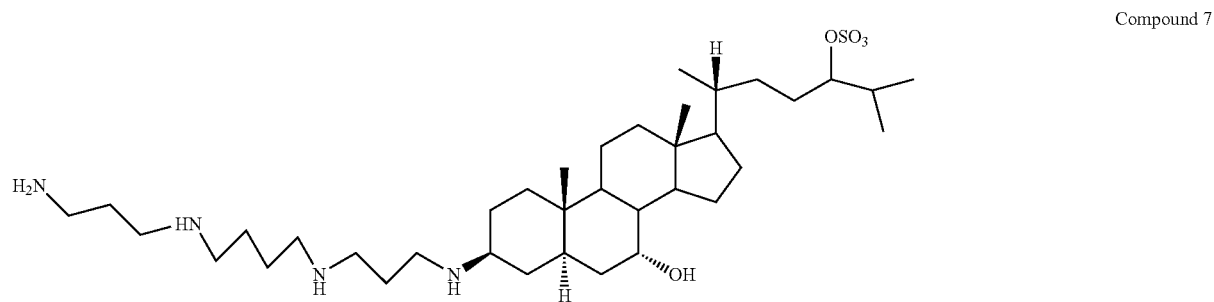

-continued

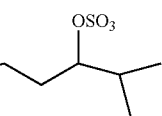

Compound 8

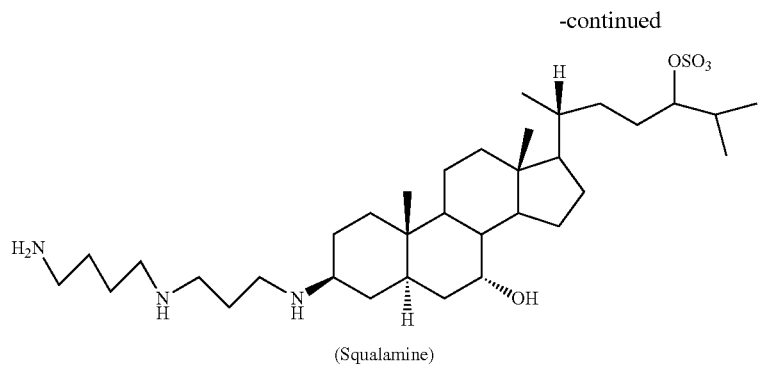

(Squalamine)

In one embodiment, the aminosterol is Aminosterol 1436 or a squalamine isomer.

In yet another embodiment of the invention, the aminosterol is a derivative of squalamine or another naturally occurring aminosterol modified through medical chemistry to improve biodistribution, ease of administration, metabolic stability, or any combination thereof. In another embodiment, the squalamine or aminosterol is modified to include one or more of the following: (1) substitutions of the sulfate by a sulfonate, phosphate, carboxylate, or other anionic moiety chosen to circumvent metabolic removal of the sulfate moiety and oxidation of the cholesterol side chain; (2) replacement of a hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system.

In yet another embodiment, the aminosterol comprises a sterol nucleus and a polyamine, attached at any position on the sterol, such that the molecule exhibits a net charge of at least +1, the charge being contributed by the polyamine.

In yet another embodiment, the aminosterol comprises a bile acid nucleus and a polyamine, attached at any position on the bile acid, such that the molecule exhibits a net positive charge being contributed by the polyamine.

In certain embodiments of the invention, the methods comprise administering squalamine or a derivative thereof at an effective daily dosing amount of about 0.1 to about 20 mg/kg body weight. In certain embodiments, the effective dose can be established by defining the initial dose required to induce the Aminosterol-Induced GI Response, i.e., the initial dose required to stimulate nausea and secretory diarrhea.

The composition can be administered via any pharmaceutically acceptable method, including but not limited to oral administration.

The methods of the invention can further comprise administering the squalamine or derivative thereof in combination with at least one additional active agent to achieve either an additive or synergistic effect. Such an additional agent can administered via a method selected from the group consisting of concomitantly, as an admixture, separately and simultaneously or concurrently, and separately and sequentially.

In one embodiment of the invention, the oral dosage form is a liquid, capsule, or tablet designed to disintegrate in either the stomach, upper small intestine, or more distal portions of the intestine with a dissolution rate appropriate to achieve the intended therapeutic benefit.

In another embodiment of the invention, essentially no aminosterol is detected in the blood stream of the subject following oral administration.

Both the foregoing summary of the invention and the following detailed description of the invention are exemplary and explanatory and are intended to provide further details of the invention as claimed. Other objects, advantages, and novel features will be readily apparent to those skilled in the art from the following detailed description of the invention.

DESCRIPTION OF THE FIGURES

FIG. 1A shows a representative trace of a suction electrode multiunit recording. The insert in FIG. 1A shows extracellular action potential (40 µV) on a faster timebase (1 ms). FIG. 1C shows the before and after data of spike frequencies averaged over 3 min for 5 separate experiments. The Control represents background discharge before applying squalamine, and the Peak gives the average firing frequency during a 3 min period at the peak of the response.

DETAILED DESCRIPTION OF THE INVENTION

Figure 1A:
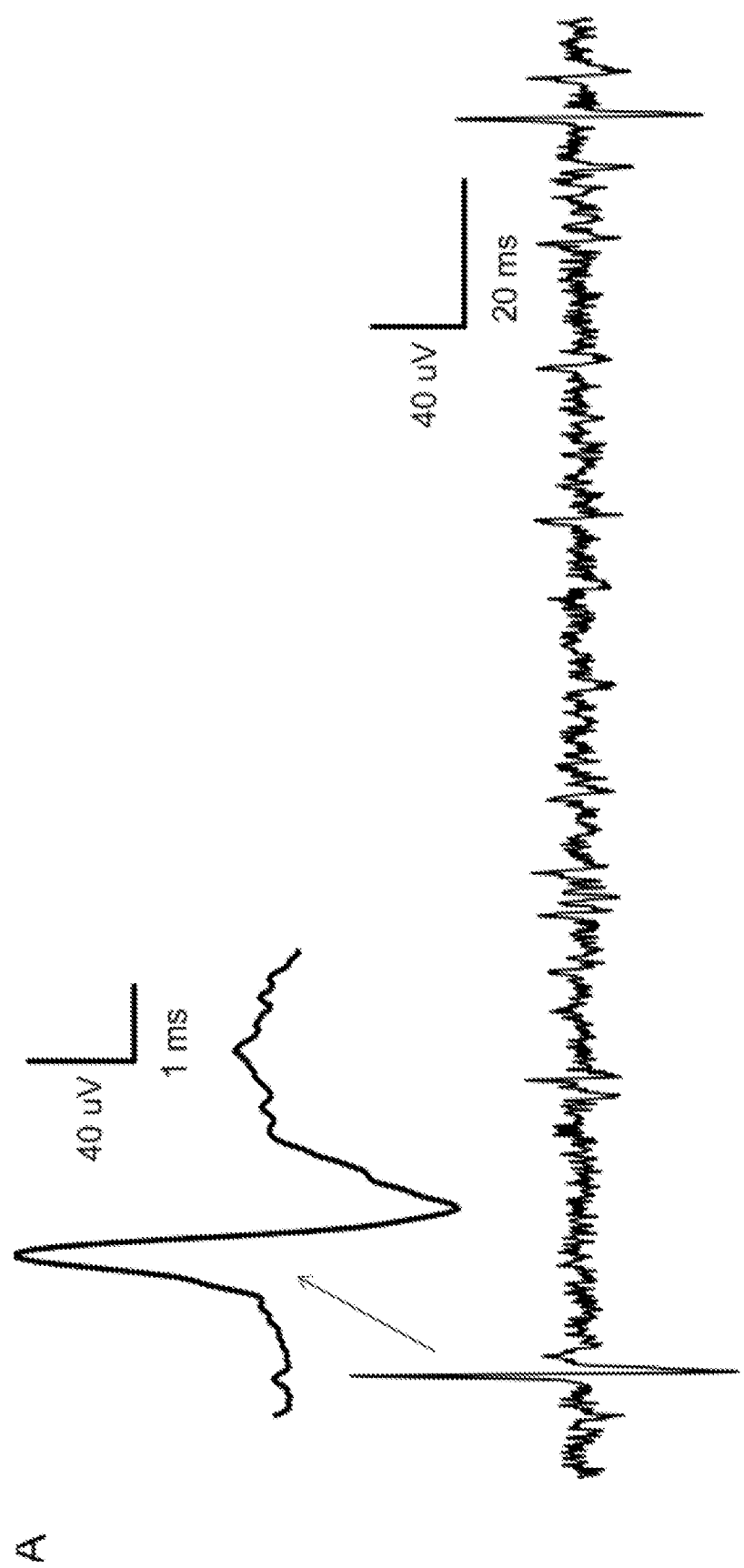
FIG. 1A shows that intraluminal squalamine increases mesenteric nerve firing frequency.

The present invention is directed to methods of stimulating a stereotyped pharmacological response in the human gastro-intestinal tract following oral administration of squalamine or a derivative thereof, or Aminosterol 1436 or a derivative thereof (Aminosterol Induced GI Response). The invention is unexpected and surprising based on the known and predicted properties of aminosterols, including squalamine and Aminosterol 1436. In particular, the invention permits exerting pharmacologic control over the enteric nervous system in a manner that is without precedent in the literature. The utility afforded by this capability includes all applications in which activation of the enteric system in this fashion could have benefit. These applications include GI conditions that would benefit from the imposition of a period of small intestinal "quieting," resembling what is commonly called an "ileal brake," or from direct effects on the enteric nervous system of amino-sterol specific activation imposed by Aminosterol administration.

An example of a condition that can be treated with a method according to the invention includes diabetes, where the delayed transit of food through the small intestine would reduce the rate of nutrient absorption and secondarily reduce stress on the endocrine pancreas. Other conditions that can be treated using a method according to the invention include irritable bowel syndrome, Opioid-induced constipation, and inflammatory bowel disease, where relaxation of the smooth muscle of the small intestine would provide relief of cramping peristaltic activity. Yet other conditions that can be treated with a method according to the invention include neurodegenerative diseases which would benefit from the direct effects of the aminosterols on the enteric neurons and their communication with immune cells within the lamina propria, as well as the stimulation of vagal afferents that track to higher centers of the central nervous system, such as Parkinson's disease, Alzheimer's disease, Huntington's chorea, neuropathy of diabetes, peripheral sensory neuropathy, traumatic head and/or spine injury, stroke, Amyotrophic lateral sclerosis, multiple sclerosis, depression, epilepsy and autism. Finally, methods according to the invention are also useful in treating and preventing a variety of malignancies, including for example, any vascularized malignancy, such as a malignancy of the colon, pancreas, liver, brain, male and female genitourinary tract, lymphatic and blood tissues, lungs, skin, breast, and endometrium. Unanticipated benefits include regression of malignancies.

I. Definitions

The following definitions are provided to facilitate understanding of certain terms used throughout this specification.

As used herein the term "aminosterol" encompasses squalamine or a derivative thereof, an isomer or prodrug of squalamine, Aminosterol 1436 or a derivative thereof, an isomer or prodrug of Aminosterol 1436, or a naturally occurring aminosterol isolated from *Squalus acanthias* or a derivative thereof, as described herein. "Aminosterols" useful in the invention also encompass a pharmaceutically equivalent salt of any aminosterol compound described herein. These compounds, and pharmaceutically acceptable salts thereof, are collectively referred to herein as "squalamine" and "aminosterols." Thus, the term "aminosterol" as used herein is intended to encompass the broader class that includes both squalamine and the known naturally occurring aminosterols.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture.

As used herein, the phrase "therapeutically effective amount" shall mean the drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

II. Mechanism of Action

The Mechanism of Action.

It has been reported that squalamine exerts its effects at the cellular level by displacing proteins bound electrostatically to negatively charged membranes, causing pleiotropic changes in the functional state of the cell. See Alexander et al., "Membrane surface charge dictates the structure and function of the epithelial na+/h+ exchanger," *EMBO J.*, 30:679-691(2011); Yeung et al., "Membrane phosphatidylserine regulates surface charge and protein localization," Science, 319(5860): 210-3 (2008); Sumioka et al., "TARP phosphorylation regulates synaptic AMPA receptors through lipid bilayers," Neuron, 66(5): 755-67 (2009); and Zasloff et al., "Squalamine as a broad-spectrum systemic antiviral agent with therapeutic potential," *Proc. Natl. Acad. Sci. USA*, 108(38): 15978-83 (2011). With respect to the disclosed invention, it is believed that squalamine and other aminosterols, such as Aminosterol 1436, are transported into the intestinal enterocyte. The presence of the aminosterol induces a response within the enterocyte, including effects on water and salt reabsorption. The aminosterol is then transported into the lamina propria where it then enters certain neurons of the enteric nervous system (via specific transporters) and induces electrical activation, ultimately, by the electrostatic mechanism proposed. The bulk of the aminosterol is then likely pumped back into the intestinal lumen, wherein it is excreted in the feces.

Squalamine is known to gain access to nerve cells, neutralize the negative electrostatic surface potential of these cells, and alter electrical channel activity (Sumioka et al., 2009). It is assumed that squalamine can access and influence the behavior of the neurons of the enteric nervous system in a fashion similar to what has been observed in cortical granular neurons (Sumioka et al., 2009). In addition, squalamine is known to inhibit the sodium hydrogen exchanger involved in water and salt reabsorption in the human small intestine by the same mechanism (Alexander et al. 2011).

As described in Example 3 below, optimal oral dosing appears to be on an empty stomach. Squalamine, because of its physical properties, is expected to bind tightly to foodstuff, and be unavailable to interact with the intestinal epithelium. Only as the food material is digested is squalamine freed. Such would be occurring in the more distal intestine.

Based on the stereotyped nature of the response and known properties of certain human gastrointestinal hormones and the communication known to exist between the human GI tract and the central nervous system, the physiological events that underlie the Aminosterol Induced GI Response can be detailed. The observed response can be divided into 3 phases.

Phase I: Nausea.

This phase begins within about 1 to about 3 hours following oral ingestion of an aminosterol, and lasts about 30 minutes. Phases II and III (see below) can be induced at doses below that required to stimulate a conscious sensation of nausea, so the conscious experience is not a required component of the overall Aminosterol Induced GI Response. The dose required to induce nausea is greater than that required to initiate Phases II and III. It is proposed that the sensation of nausea after administration of squalamine or aminosterol 1436 is a consequence of the direct stimulation of the brainstem via vagal afferents stimulated within the intestinal wall. The stereotyped nature of the response and the predictability of its temporal duration, suggest that the aminosterol stimulates a specific set of enteric neurons via a specific mechanism. Were the nausea an effect secondary to non-specific mucosal injury, it would be expected to be more variable in both intensity, onset of appearance, and duration.

Based on the timing of the nausea, the site of action is likely the proximal small intestine, the duodenum, and/or the jejunum. It is possible that nausea experienced at higher doses of aminosterols results from the discharge of intestinal Enterochromaffin cells, which release histamine and serotonin, the L-cells (GLP-1), the K-cells (GIP), and the I-cells (CCK), each releasing hormones that are known to circulate systemically, exhibit a brief lifetime in the blood stream, and cause nausea.

In Example 6 it is shown that orally administered squalamine does not induce release of GLP-1 into the blood stream of a healthy human, and thus it is likely that Phase I results from vagal afferent stimulation of the nausea centers in the brain. This explanation is supported by Example 10 (FIG. 1), where it is shown that application of squalamine to the mouse colon leads to the stimulation of electrical signals flowing through the afferent arm of the vagus.

Phase II: Net Fluid Loss from the Intestine:

If a sufficiently large dose of aminosterol is administered orally, the subject will experience the discharge rectally of a small volume of watery fluid. The discharge is clear, watery in nature and reflects either an increased secretory response or decreased absorptive response of the intestine with respect to its handling of the fluxes of fluid within the lumen. VIP (vasoactive intestinal peptide) is a well characterized neuropeptide, present within the enteric nervous system and well known to provoke this type of secretory response. It is presumed that the discharge of the enteric nervous system in Phase I triggers the activation of VIP expressing neurons within the enteric nervous system, resulting in the alteration of fluid handling by the enterocytes within the jejunum. Alternatively, the aminosterol could inhibit the sodium-hydrogen exchanger type III (NHE-3) expressed on the lumenal surface of the enterocytes, which is the major transporter responsible for the absorption of sodium and water from the intestine.

It has previously been reported that squalamine inhibits the NHE-3 transporter by an electrostatic mechanism, where squalamine enters an epithelial cell via a specific transporter (Alexander et al. 2011), and this is the same mechanism described above with respect to the claimed method. To access the enteric nervous system, the aminosterol must first cross the epithelial layer that separates the lumen of the intestine from the wall of the bowel, where the neurons of the enteric nervous system are situated. It is presumed that squalamine, and other active aminosterols, cross the epithelium principally through the transport into the epithelial cell, followed by the subsequent exiting of the molecule from that cell. During the period of time squalamine remains in the cell (and likely for some time after), it is expected that the NHE-3 transporter is inhibited, and effects on fluid flux within that segment of intestine accordingly affected. The duration of the response and the reproducible volume released suggests that the response is self-limiting, possibly through a negative/inhibitory feedback loop involving the eneteric nervous system, or as a consequence of the clearance from the epithelial cell of the compound and the subsequent restoration of normal function. Regardless of the mechanism, the stereotypic and dose-dependent nature of the secretory response suggest that the administration of the aminosterol stimulates the small intestine in a highly specific fashion.

Phase III: Intestinal Motility.

Squalamine has distinct pharmacological effects on both small and large intestinal motility and muscle tone. Following the watery discharge, the bowel enters a period of "quiet" that lasts between 2-3 days, following the larger squalamine dose (for example 200 mg, although other larger doses as described herein can be used). At lower squalamine doses, the period of "quiet" is reduced proportionally in duration. During this period the bowel is not inactive ("ileus") as it would be following oral administration of an opioid narcotic. There are bowel sounds, and gas is passed intermittently. Appetite is nearly normal, although it could in principal be slightly reduced. Gastric fullness after a meal is sensed. During this phase, one does not experience bloating, abdominal discomfort, abdominal pain, nausea, or a sense of fullness. The delay in the passage of a stool will be recognized as "unusual" in an individual with a more frequent bowel pattern. This phase ends with passage without urgency of a soft stool, in contrast to what would have been observed following a period of "constipation." This phase is either a direct effect of squalamine on the enteric nervous system, progressively stimulating the enteric nervous system as the compound moves rectally, and/or a result of the activation of the brain by the presence of squalamine within the gut resulting in efferent signals directed by the brain that alter the motility of the intestines.

This Phase is reminiscent of the condition of reduced gut motility termed an "ileal brake." It is designed physiologically to slow gut motility to enhance nutrient extraction. Certain gut hormones, such as GLP-1, exhibit this pharmacological activity. Indeed, the benefits of GLP-1 and its analogs in the treatment of diabetes mellitus in large part are believed to derive from the ability of GLP-1 and analogs thereof to slow entry of nutrients from the intestine into the liver, and thereby reduce the secretory rate of insulin required to match the influx of nutrients. However, as shown in Example 6, oral administration of squalamine does not stimulate release of GLP-1 as measured in the blood stream. It can also be explained as a consequence of the activation of VIP-nergic neurons within the enteric nervous. The release of VIP from these neurons is directed at the muscle layers of the bowel wall and has a known relaxing effect on muscular contractions of the intestine. It is believed that this mechanism is the most plausible. This mechanism could arise via direct stimulation of these neurons by the presence of squalamine, or indirectly, via the stimulation of specific signals from the enteric nervous system directed to the brain, which in turn sends out signals that release VIP from enteric nerves.

Since squalamine is not absorbed from the GI tract, it moves slowly toward the rectum following oral ingestion. As squalamine proceeds distally within the small intestine, squalamine stimulates the underlying epithelium (increasing the fluid content of the lumen) and stimulates the underlying enteric nervous system. Over the course of about 2 to about 3 days, the movement of squalamine into the colon and eventually its excretion in feces leads to the termination of its pharmacological activity and restoration of prior bowel function.

The effects of squalamine on the colon appear to differ from those on the small intestine. In particular, it appears that squalamine increases colonic motility as part of the Aminosterol-induced GI response, based on the soft nature of the stool produced in a treated human. In addition, studies in the mouse (Example 11, FIG. 2) confirm that squalamine stimulates colonic motility. Thus, while small intestinal motility appears to be slowed, colonic motility appears to be increased, with a compensatory adjustment of net fluid flux within the bowel to maintain a stool of normal consistency.

III. Beneficial Consequences of the Aminosterol-Induced GI Response

Based on the unanticipated pharmacological response of the GI tract to oral administration of squalamine, several unexpected and unprecedented applications can be understood.

Chronic Idiopathic Constipation, Opioid-Induced Constipation, Irritable Bowel Syndrome and Inflammatory Bowel Disease:

The fundamental etiology of these common conditions is not known. Two broad categories of Irritable Bowel Syndrome exist, one characterized by diarrhea, the other by constipation. Amongst the more effective of the treatments are serotonin analogs that act on the enteric nervous system to either stimulate mobility (in the constipation form) or inhibit it (in the diarrheal form). Treatment of IBS with an oral aminosterol could "reboot" the enteric nervous system. Clearly, in the case of the diarrheal form, administration should impose an about 2 to about 5 day period of bowel rest/silence that would be expected to reduce small intestinal transit. In the case of the constipation type, the imposition of a muscle-relaxing effect on the small intestine and a stimulation of colonic mobility of the GI tract could introduce normalcy. The stimulation of net intestinal secretion along with imposition of the "controlled" motility patterns of the small and large intestines would provide benefit in the setting of chronic constipation. Similarly, a method according to the invention can provide benefit in the setting of opioid-induced constipation, where secretion is inhibited, peristaltic contractions become uncoordinated, and colonic motility is markedly reduced, as oral aminosterol administration should address these issues.

Diabetes Mellitus:

The use of GLP-1 analogs in the treatment of diabetes has been well established. These compounds reduce the insulin requirement and tend to smooth out overall insulin titration. The mechanism by which the GLP-1 compound class produces their benefit remains controversial, with some arguments presented in support of promoting insulin secretion, while other arguments support the beneficial effects of the "ileal brake." Thus, the method according to the invention utilizing oral administration of one or more aminosterols, to trigger the Aminosterol-Induced GI Response, should prove beneficial along with insulin/and insulin secretagogues in the management of Diabetes mellitus.

Neurodegenerative Disorders:

The proposed mechanism by which squalamine provokes the Aminosterol Induced GI Response involves the direct stimulation of nerves within the enteric nervous system, and stimulation of currents flowing towards the brain through afferent nerves of the vagus. Stimulation of afferents of the vagus, which distribute to centers and tracts within the brain would be expected to stimulate release of a suite of neuropeptides within the brain itself. The continued imposition of the ileal brake for several days following aminosterol dosing, speaks to the length of time the aminosterol-provoked gut/CNS interaction must be operative following a single dose of squalamine.

In addition, the entry of squalamine into the nerves of the enteric nervous system could provide direct benefit in degenerative conditions where accumulation of certain proteins is believed to be causally involved. Specifically, in Parkinson's disease, the accumulation of alpha synuclein is believed to play a role in the neuronal damage associated with the condition. Alpha synuclein is a protein with a cationic N-terminus and can interact electrostatically with the internal membranes of the nerve cell in which it is expressed. Since squalamine can both enter nerve cells and neutralize the negative surface potential of these membrane surfaces, squalamine and related aminosterols have the capacity to displace alpha synuclein from membrane sites within nerves, and as a consequence, interrupt the pathophysiology of the disease. This principle is demonstrated in Example 14.

Cancer Therapy:

The complex interactions between the epithelial cells and enteric neurons suggest that the methods of the invention can influence the growth and spread of cancer. Recent studies in both animals and man have strongly suggested that malignant tumors must establish communication with the autonomic nervous system. The enhanced flux of electrical signals emanating from the squalamine-stimulated enteric nervous system could disrupt effective communication between a malignant tumor and the divisions of the autonomic nervous system. Indeed, as shown in Examples 14-19, the induction of the Aminosterol Induced GI Response is associated with striking regression of currently untreatable malignancies, under conditions where squalamine itself does not enter the bloodstream, and therefore the aminosterol must be acting in an indirect fashion. Examples of malignancies that can be treated using the methods of the invention include, but are not limited to, vascularized malignancies, and/or malignancies of the colon, pancreas, liver, brain, male and female genitourinary tract, lymphatic and blood tissues, lungs, skin, breast, and endometrium. All of these cancers are known to be influenced by metastatic spread through the lymphatic and vascular systems, a process which we believe to be influenced by the action of the autonomic nervous system.

Thus, the invention disclosed herein teaches how to stimulate the enteric nervous system to achieve certain beneficial effects in many different diseases and leads to the possibility that by administering an aminosterol such as squalamine or a derivative thereof under conditions that provoke the Aminosterol-Induced GI Response, neuroprotective benefits can accrue to an individual so treated.

The conditions referred to are those in which the induction of neuro-protective hormones could provide preventative or therapeutic benefit. These conditions include, for example, Parkinson's disease, Alzheimer's disease, Stroke, Amyotrophic lateral sclerosis, Acute traumatic injury to the central nervous system, including the spinal cord, neurodegenerative processes of aging, early stages of cerebral palsy, epilepsy, peripheral sensory neuropathy, diabetic neuropathy, Huntington's chorea, Multiple sclerosis, depression and autism. In addition, by administering squalamine under conditions that provoke the Aminosterol-Induced GI Response, certain human malignancies can be induced to regress, in a setting where orally administered squalamine has not entered the bloodstream.

Experiments in animal models of neurodegenerative disease have demonstrated the neuro-protective benefits of several of the neuropeptides likely to be released within the nervous system during the unfolding Aminosterol-Induced GI Response. These include:

Vasoactive intestinal peptide: Alzheimer's (White et al. 2010); Parkinson's (Delgado and Ganea, 2003); Head trauma (Gressens, Marret et al, 1997); multiple sclerosis (Gonzalez-Rey, Fernandez-Martin et al. 2006)

GLP-1: Parkinson's (Li, Perry et al. 2009); head trauma (Li, Perry et al. 2009); Alzheimer's (Li, Perry et al. 2009).

CCK: Epilepsy (Tirassa, Costa et al. 2005)

Clinical studies in man have demonstrated the benefits of vagal nerve stimulation in several disorders, and as a consequence of vagal afferent activity induced by the Aminoterol-Induced GI Response, several conditions can be considered for which oral aminosterol administration could provide clinical benefit, such as depression, epilepsy and autism.

IV. Beneficial Pharmacological Properties of the Aminosterols as Stimulants of the Aminosterol-Induced GI Response Aminosterols, such as squalamine and derivatives thereof, including but not limited to Aminosterol 1436, are not absorbed from the gastrointestinal tract of mammals, including man. As a consequence, this invention teaches how to stimulate the Aminosterol-Induced GI Response without introducing aminosterols into the human systemic circulation. This is significant, as toxicities known to be associated with, for example, injectable administration of Aminosterols and derivatives thereof, are not a concern for the uses disclosed in this invention. In addition, issues relating to potential toxicities not as yet known (effects on fertility, etc) would be of lesser concern with the oral administration protocol of the invention.

In one embodiment of the invention, following oral administration there is essentially no detectable levels of the administered aminosterol in the bloodstream of the subject. In another embodiment of the invention, following oral administration there is preferably less than about 10 ng/ml of the administered aminosterol in the bloodstream of the subject, measured between about 1-about 12 hours following oral administration.

Retention of the aminosterols within the lumen of the intestine permits optimal orchestration of the Aminosterol-Induced GI Response. As the effects on intestinal motility that characterize Phase III are actuated, and gut motility within the small intestine is slowed, the passage distally of the aminosterol is slowed. Thus, the intensity of the Aminosterol-Induced GI Response will be maintained by "a positive feedback loop," whereby the slowing of small intestinal motility extends the duration of effect until it reaches the colon, where it is finally expelled, resulting in the termination of the Aminosterol-Induced GI Response.

Repeat dosing regimens are timed by the rate of clearance of the aminosterol from the intestine. It is assumed that at a certain time after the initial "loading" dose, surface concentrations of the aminosterol will decrease as the substance spreads across the surface of the intestinal walls and progresses distally. In the examples described below, the Aminosterol-Induced GI Response appears to last about 4 days following a single 200 mg oral dose of squalamine or Aminosterol 1436. A second dose on day 4 of about 100 mg, followed by successive about 100 mg dosing every 4 days, would represent one reasonable regimen designed to maintain a steady state surface concentration in the intestine.

Effective dosing regimens can also be clinically established based on the dose required to observe a change in bowel behavior at least about 1-about 2 hours following oral dosing. A change in bowel behavior includes a change in the normal frequency of defecation, the consistency of the stools, the perceived activity of the bowels, nausea, or the passage of a watery rectal discharge. An effective oral dose generally falls between about 10 mg to about 400 mg.

Dosing can be once daily, or divided over multiple time periods during the day.

Exemplary dosing regimens include, but are not limited to: (1) Initiating with a "low" initial daily dose, and gradually increasing the daily dose until a dose is reached that elicits evidence of the activation of the enteric nervous system, where the "low" dose is from about 10-about 100 mg per person, and the final effective daily dose is between about 25-about 1000 mg/person; (2) Initiating with a "high" initial dose, which necessarily stimulates the enteric nervous system, and reducing the subsequent daily dosing to that required to elicit a clinically acceptable change in bowel behavior, with the "high" daily dose being between about 50-about 1000 mg/person, and the subsequent lower daily oral dose being between about 25-about 500 mg/person; (3) Periodic dosing, where an effective dose can be delivered once every about 2, about 3, about 4, about 5, about 6 days, or once weekly, with the initial dose determined to capable of eliciting an Aminosterol Induced Response Oral dosing should continue at least until the clinical condition has resolved. To establish the need for continued dosing, treatment can be discontinued and the condition revaluated. If necessary, oral administration should be resumed. The period of oral dosing can be for about 1, about 2, about 3, or about 4 weeks; about 1, about 2, about 3, about 4, about 5, about 6, about 7, about 8, about 9, about 10, about 11, or about 12 months, or about 1, about 2, about 3, about 4, or 5 years, or longer.

Failure to elicit an Aminosterol-Induced GI Response would suggest that the dose being administered was inadequate, and would suggest continued titration until the GI response is observed. Dosing could proceed from a lower to higher dose, with the GI responses to daily increases monitored. An effective dose would be that which induced the complete GI response. An excessive Aminosterol-Induced GI Response at a low doses would speak to a sensitivity and would guide appropriate administration at lower doses.

The sensitivity of the Aminosterol-Induced GI Response to oral administration of aminosterols is likely due to several variables: (1) The absorption of the aminosterol into a mucous layer, an effect that would reduce free concentration of aminosterol available for diffusion onto the epithelial surface, thereby reducing the response to a given oral dose; and (2) an increase in the permeability of the epithelial wall (leakiness), which occurs following infections, allergic enteropathies, and in states of intestinal inflammation. In such settings, the normal transport of the aminosterol across the epithelium, which is facilitated by the controlled entry and subsequent exit of the molecule from the lining epithelial cell, would be circumvented. Compound would leak across the epithelial barrier, and expose the nerve network within the bowel wall to abnormally high concentrations. Hence, an excessive response might provide a diagnostic impression of the permeability status of the epithelium.

V. Compositions Useful in the Methods of the Invention

The invention relates to methods of treating conditions that benefit from stimulation of the Aminosterol-Induced GI Response. The methods comprise orally administering a therapeutically effective amount of one or more aminosterols or a pharmaceutically equivalent salt thereof to a subject in need. A "subject in need" is a human or animal at risk of or suffering from conditions including, but not limited to, Irritable bowel syndrome, Opioid-induced constipation, Inflammatory Bowel Disease, Diabetes mellitus, Parkinson's disease, Alzheimer's disease, dementia of aging, Huntington's chorea, neuropathy of diabetes, peripheral sensory neuropathy, traumatic head and/or spine injury, stroke, Amyotrophic lateral sclerosis, multiple sclerosis, depression, epilepsy and autism. In addition, by orally administering an aminosterol under conditions that provoke the Aminosterol-Induced GI Response, certain human malignancies can be induced to regress, in a setting where the aminosterol has not entered the bloodstream. Similarly, chronic oral administration of one or more aminosterols should prevent the appearance of malignancy.

U.S. Pat. No. 6,962,909, for "Treatment of neovascularization disorders with squalamine" to Zasloff et al., discloses various aminosterols, the disclosure of which is specifically incorporated by reference. Any aminosterol known in the art, including those described in U.S. Pat. No. 6,962,909, can be used in this invention, as long as the aminosterol carries a net positive charge of at least +1 created by a polyamine moiety.

In yet another embodiment, the aminosterol comprises a bile acid nucleus and a polyamine, attached at any position on the bile acid, such that the molecule exhibits a net positive charge being contributed by the polyamine.

In another embodiment, the invention encompasses methods of treating conditions described herein comprising orally administering a therapeutically effective amount of one or more aminosterols that can inhibit the formation of actin stress fibers in endothelial cells stimulated by a ligand known to induce stress fiber formation. The aminosterols can have the chemical structure of Formula I:

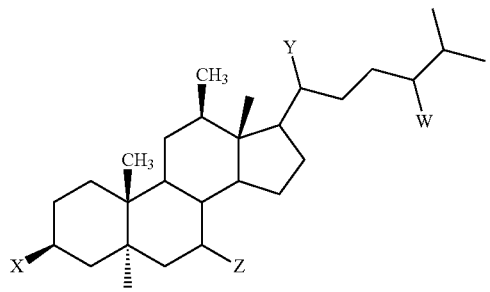

wherein,
W is 24S—$OSO_3$ or 24R—$OSO_3$;
X is 3β-$H_2N$—$(CH_2)_4$—NH—$(CH_2)_3$—NH— or 3α-$H_2N$—$(CH_2)_4$—NH—$(CH_2)_3$—NH—;
Y is 20R— $CH_3$; and
Z is 7α or 7β-OH.

Exemplary aminosterols that can be used in the methods of the invention include, but are not limited to, the known aminosterols (compounds 1-8) isolated from *Squalus acanthias*:

Compound 1

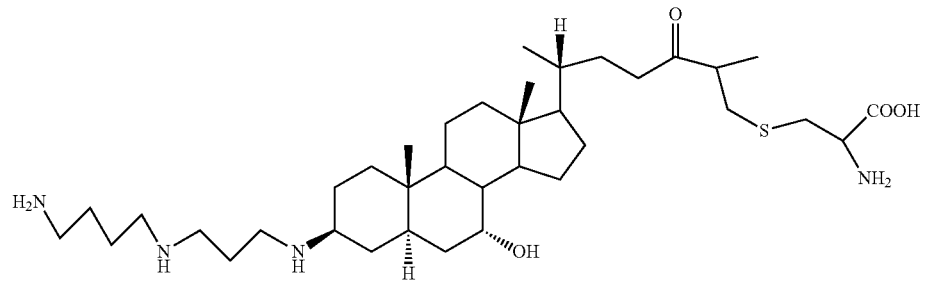

Compound 2

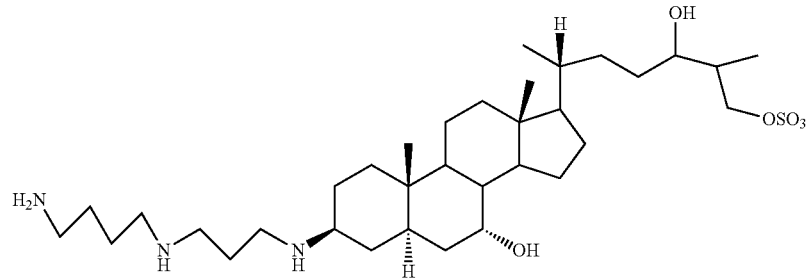

Compound 3

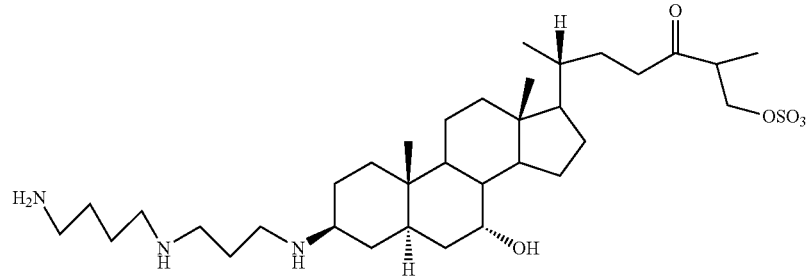

-continued

Compound 4

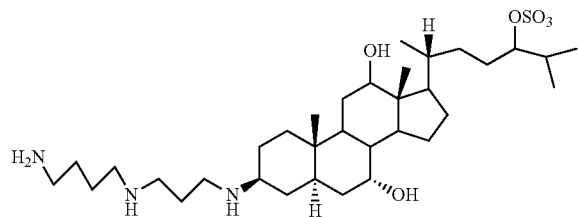

Compound 5

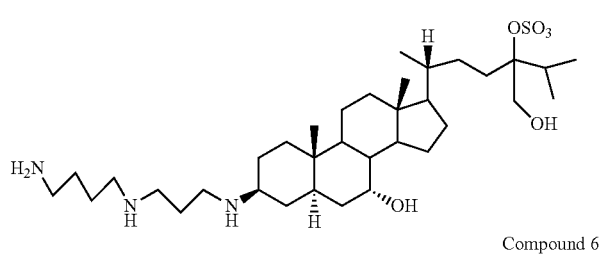

Compound 6

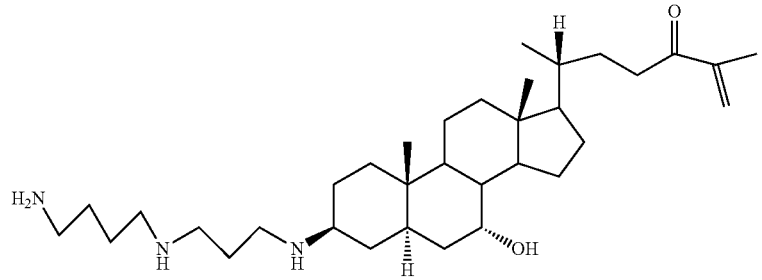

Compound 7

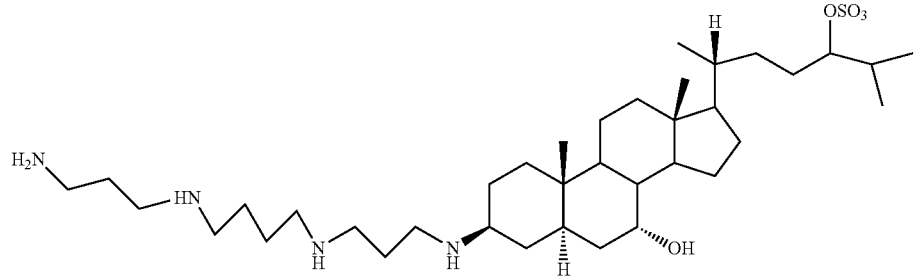

Compound 8

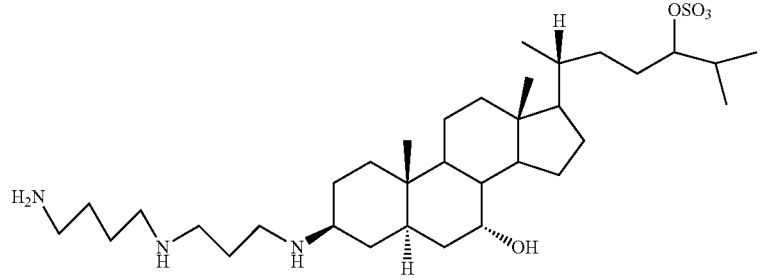

(Squalamine)

A variant or derivative of squalamine may have one or more chemical modifications which do not modify the activity of squalamine. Similarly, analogous modifications can be made to the other known naturally occurring aminosterols described above. A "variant" or "derivative" of squalamine or a naturally occurring aminosterol in which modifications well known in the art of medicinal chemistry to "mimic" the original spatial and charge characteristics of a portion of the original structure have been introduced to improve the therapeutic characteristics of the aminosterol. In general, such modifications are introduced to influence metabolism and biodistribution. Examples of such variants or derivatives include, but are not limited to, (1) substitutions of the sulfate by a sulfonate, phosphate, carboxylate, or other anionic moiety chosen to circumvent metabolic removal of the sulfate moiety and oxidation of the cholesterol side chain; (2) replacement of an hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system.

The compositions useful in the methods of the invention comprise at least one aminosterol. In one embodiment, the compositions used in the methods of the invention comprise: (a) at least one pharmaceutical grade aminosterol; and optionally (b) at least one phosphate selected from the group consisting of an inorganic phosphate, an inorganic pyrophosphate, and an organic phosphate, wherein the aminosterol is formulated as a weakly water soluble salt of the phosphate. In another embodiment of the invention, the phosphate is an inorganic polyphosphate, and the number of phosphates can range from 3 (tripolyphosphate) to 400. In yet another embodiment, the phosphate is an organic phosphate which comprises glycerol 2 phosphates. In yet another embodiment, the aminosterol is selected from the group consisting of: (a) squalamine or a pharmaceutically acceptable salt or derivative thereof; (b) a squalamine isomer; (c) Aminosterol 1436; (d) an aminosterol comprising a sterol or bile acid nucleus and a polyamine, attached at any position on the sterol or bile acid, such that the molecule exhibits a net charge of at least +1, the charge being contributed by the polyamine; (e) an aminosterol which is a derivative of squalamine modified through medical chemistry to improve biodistribution, ease of administration, metabolic stability, or any combination thereof; (f) an aminosterol modified to include one or more of the following: (i) substitutions of the sulfate by a sulfonate, phosphate, carboxylate, or other anionic moiety chosen to circumvent metabolic removal of the sulfate moiety and oxidation of the cholesterol side chain; (ii) replacement of a hydroxyl group by a non-metabolizable polar substituent, such as a fluorine atom, to prevent its metabolic oxidation or conjugation; and (iii) substitution of various ring hydrogen atoms to prevent oxidative or reductive metabolism of the steroid ring system; (g) an aminosterol that can inhibit the formation of actin stress fibers in endothelial cells stimulated by a ligand known to induce stress fiber formation, having the chemical structure of Formula I (above).

In one embodiment, the methods of the invention can employ a formulation of Aminosterol 1436 (Zasloff, Williams et al. 2001) as an insoluble salt of phosphate, polyphosphate, or an organic phosphate ester. In another embodiment, the aminosterol can be composed of a sterol or bile acid nucleus to which a polyamine is chemically linked, displaying a net positive charge of at least +1. The invention can be embodied in a formulation comprising a phosphate suspension or as a tablet for oral administration. As an oral formulation, squalamine phosphate would slowly dissolve in the gastrointestinal tract, and not subject the lining of the intestine to high local concentrations that would otherwise irritate or damage the organ.

Dosage Forms.

The formulations may conveniently be presented in unit dosage form and may be prepared by any of the methods well known in the art of pharmacy. Any pharmaceutically acceptable dosage form may be employed in the methods of the invention For example, the composition can be formulated into a dosage form (a) selected from the group consisting of liquid dispersions, gels, aerosols, lyophilized formulations, tablets, capsules; and/or (b) into a dosage form selected from the group consisting of controlled release formulations, fast melt formulations, delayed release formulations, extended release formulations, pulsatile release formulations, and mixed immediate release and controlled release formulations; or (c) any combination of (a) and (b).

An exemplary dosage form is an orally administered dosage form, such as a tablet or capsule. Such methods include the step of bringing into association the aminosterol with the carrier that constitutes one or more accessory ingredients. In general, the formulations are prepared by uniformly and intimately bringing into association the active ingredient with liquid carriers or finely divided solid carriers or both, and then, if necessary, shaping the product.

Formulations or compositions of the invention may be packaged together with, or included in a kit with, instructions or a package insert. For instance, such instructions or package inserts may address recommended storage conditions, such as time, temperature and light, taking into account the shelf-life of the aminosterol. Such instructions or package inserts may also address the particular advantages of the aminosterol, such as the ease of storage for formulations that may require use in the field, outside of controlled hospital, clinic or office conditions.

The aminosterol composition can also be included in nutraceuticals. For instance, the aminosterol composition may be administered in natural products, including milk or milk product obtained from a transgenic mammal which expresses alpha-fetoprotein fusion protein. Such compositions can also include plant or plant products obtained from a transgenic plant which expresses the aminosterol. The aminosterol can also be provided in powder or tablet form, with or without other known additives, carriers, fillers and diluents. Exemplary nutraceuticals are described in Scott Hegenhart, Food Product Design, December 1993.

The aminosterol composition will be formulated and dosed in a fashion consistent with good medical practice, taking into account the clinical condition of the individual patient (especially the side effects of treatment with the aminosterol alone), the method of administration, the scheduling of administration, and other factors known to practitioners. The "effective amount" for purposes herein is thus determined by such considerations.

Effective dosing regimens can be based on that dose required to observe a change in bowel behavior at least about 1-about 2 hours following oral dosing. A change in bowel behavior includes a change in the normal frequency of defecation, the consistency of the stools, the perceived activity of the bowels, nausea, or the passage of a watery rectal discharge. An effective oral dose generally falls between about 10 mg to about 400 mg Dosing can be once daily, or divided over multiple time periods during the day.

Effective dosing regimens can in part be established by measuring the rate of excretion of the orally administered aminosterol and correlating this with clinical symptoms and signs. Exemplary dosing regimens include, but are not limited to: (1) Initiating with a "low" initial daily dose, and gradually increasing the daily dose until a dose is reached that elicits evidence of the activation of the enteric nervous system, where the "low" dose is from about 10-about 100 mg per person, and the final effective daily dose is between about 25-about 1000 mg/person; (2) Initiating with a "high" initial dose, which necessarily stimulates the enteric nervous system, and reducing the subsequent daily dosing to that required to elicit a clinically acceptable change in bowel behavior, with the "high" daily dose being between about 50-about 1000 mg/person, and the subsequent lower daily oral dose being between about 25-about 500 mg/person; (3) Periodic dosing, where an effective dose can be delivered once every about 2, about 3, about 4, about 5, about 6 days, or once weekly, with the initial dose determined to capable of eliciting an Aminosterol Induced Response.

Oral dosing should continue at least until the clinical condition has resolved. To establish the need for continued dosing, treatment can be discontinued and the condition revaluated. If necessary, oral administration should be resumed. The period of oral dosing can be for about 1, about 2, about 3, or about 4 weeks; about 1, about 2, about 3, about 4, about 5, about 6, about 7, about 8, about 9, about 10, about 11, or about 12 months, or about 1, about 2, about 3, about 4, or 5 years, or longer.

In other embodiments of the invention, the first or initial "large" dose of squalamine (per person) can be selected from the group consisting of about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1025, about 1050, about 1075, about 1100, about 1125, about 1150, about 1175, about 1200, about 1225, about 1250, about 1275, about 1300, about 1325, about 1350, about 1375, about 1400, about 1425, about 1450, about 1475, about 1500, about 1525, about 1550, about 1575, about 1600, about 1625, about 1650, about 1675, about 1700, about 1725, about 1750, about 1775, about 1800, about 1825, about 1850, about 1875, about 1900, about 1925, about 1950, about 1975, and about 2000 mg. In other embodiments of the invention, the second smaller dose of squalamine (per person) is less than the first or initial dose and can be selected from the group consisting of about, 10, about 25, about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, and about 1000 mg. Finally, in other embodiments of the invention, the periodic squalamine dosage (per person) can be selected from the group consisting of about 10, about 25, about 50, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, and about 1000 mg.

Any pharmaceutical used for therapeutic administration can be sterile. Sterility is readily accomplished by filtration through sterile filtration membranes (e.g., 0.2 micron membranes).

The invention also provides a pharmaceutical pack or kit comprising one or more containers filled with one or more of the ingredients of the aminosterol composition useful in the methods of the invention, including containers filled with an appropriate amount of a phosphate, either as a powder, to be dissolved, or as a sterile solution. Associated with such container(s) can be a notice in the form prescribed by a governmental agency regulating the manufacture, use or sale of pharmaceuticals or biological products, which notice reflects approval by the agency of manufacture, use or sale for human administration. In addition, the aminosterol may be employed in conjunction with other therapeutic compounds.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose, such as AVICEL® PH101 and AVICEL® PH102, microcrystalline cellulose, and silicified microcrystalline cellulose (PROSOLV SMCC™). Suitable lubricants, including agents that act on the flowability of the powder to be compressed, may include colloidal silicon dioxide, such as AEROSIL® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are MAGNASWEET® (trademark of MAFCO), bubble gum flavor, and fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as AVICEL® PH101 and AVICEL® PH102; lactose such as lactose monohydrate, lactose anhydrous, and PHARMATOSE® DCL21; dibasic calcium phosphate such as EMCOMPRESS®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof. Examples of effervescent agents include effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

Combination Therapy.

In the methods of the invention, the aminosterol compositions may be administered alone or in combination with other therapeutic agents. As noted above, the methods of the invention are useful in treating and/or preventing the conditions described herein, including but not limited to chronic idiopathic constipation, Opioid induced constipation, Irritable bowel syndrome, Inflammatory Bowel Disease, Diabetes mellitus, Parkinson's disease, Alzheimer's disease, dementia of aging, Huntington's chorea, neuropathy of diabetes, peripheral sensory neuropathy, cerebral palsy, epilepsy, diabetic neuropathy, traumatic head and/or spine injury, stroke, Amyotrophic lateral sclerosis, multiple sclerosis, and certain malignancies. Thus, any active agent known to be useful in treating these conditions can be used in the methods of the invention, and either combined with the aminosterol compositions used in the methods of the invention, or administered separately or sequentially.

For example, in methods of treating Irritable bowel syndrome, the aminosterol composition can be co-administered or combined with drugs commonly prescribed to treat IBS or related symptoms, such as alosetron hydrochloride (LOTRONEX®), fiber supplements or laxatives for constipation or medicines to decrease diarrhea, such as diphenoxylate and atropine (LOMOTIL®) or loperamide (IMODIUM®). An antispasmodic is commonly prescribed for treating IBS, which helps control colon muscle spasms and reduce abdominal pain. Antidepressants may relieve some symptoms of IBS. However, both antispasmodics and antidepressants can worsen constipation, so some doctors will also prescribe medications that relax muscles in the bladder and intestines, such as *belladonna* alkaloid combinations and phenobarbital (DONNATAL®) and chlordiazepoxide and clidinium bromide (LIBRAX®).

In methods of treating Inflammatory Bowel Disease, the aminosterol composition can be co-administered or combined with drugs commonly prescribed to treat Inflammatory Bowel Disease or related symptoms, such as aminosalicylates, corticosteroids, immune modifiers, anti-tumor necrosis factor (TNF) agents, and antibiotics. Exemplary aminosalicylates include but are not limited to sulfasalazine (AZULFIDINE®), mesalamine (ASACOLA®, PENTASA®), olsalazine (DIPENTUM®), and balsalazide (COLAZAL®). Exemplary corticosteroids include but are not limited to methylprednisolone, prednisone, prednisolone, budesonide, dexamethasone, hydrocortisone, betamethasone, cortisone, prednisolone, and triamcinolone. Exemplary immune modifiers include but are not limited to 6-mercaptopurine (6-MP, PURINETHOL®) and azathioprine (IMURAN®). An exemplary anti-TNF agent includes but is not limited to infliximab (REMICADE®). Exemplary antibiotics include but are not limited to metronidazole and ciprofloxacin. Additional examples of antibiotic agents include, but are not limited to, aminoglycosides, Ansamycins, Carbacephems, Carbapenems, Cephalosporins, Glycopeptides, Macrolides, Monobactams, Penicillins, Polypeptides, Polymyxin, Quinolones, Sulfonamides, Tetracyclines, and others (e.g., Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in US), Thiamphenicol, Tinidazole, Dapsone, and lofazimine). Examples of these classes of antibiotics include, but are not limited to, AMIKACIN®, GENTAMICIN®, KANAMYCIN®, NEOMYCIN®, NETILMICIN®, STREPTOMYCIN®, TOBRAMYCIN®, PAROMOMYCIN®, GELDANAMYCIN®, HERBIMYCIN®, LORACARBEF®, ERTAPENEM®, DORIPENEM®, IMIPENEM®/CILASTATIN®, MEROPENEM®, CEFADROXIL®, CEFAZOLIN®, CEFALOTIN® or CEFALOTHIN®, CEFALEXIN®, CEFACLOR®, CEFAMANDOLE®, CEFOXITIN®, CEFPROZIL®, CEFUROXIME®, CEFIXIME®, CEFDINIR®, CEFDITOREN®, CEFOPERAZONE®, CEFOTAXIME®, CEFPODOXIME®, CEFTAZIDIME®, CEFTIBUTEN®, CEFTIZOXIME®, CEFTRIAXONE®, CEFEPIME®, CEFTOBIPROLE®, TEICOPLANIN®, VANCOMYCIN®, AZITHROMYCIN®, CLARITHROMYCIN®, DIRITHROMYCIN®, ERYTHROMYCIN®, ROXITHROMYCIN®, TROLEANDOMYCIN®, TELITHROMYCIN®, SPECTINOMYCIN®, AZTREONAM®, AMOXICILLIN®, AMPICILLIN®, AZLOCILLIN®, CARBENICILLIN®, CLOXACILLIN®, DICLOXACILLIN®, FLUCLOXACILLIN®, MEZLOCILLIN®, METICILLIN®, NAFCILLIN®, OXACILLIN®, PENICILLIN®, PIPERACILLIN®, TICARCILLIN®, BACITRACIN®, COLISTIN®, POLYMYXIN® CIPROFLOXACIN®, ENOXACIN®, GATIFLOXACIN®, LEVOFLOXACIN®, LOMEFLOXACIN®, MOXIFLOXACIN®, NORFLOXACIN®, OFLOXACIN®, TROVAFLOXACIN®, GREPAFLOXACIN®, SPARFLOXACIN®, TEMAFLOXACIN®, MAFENIDE®, SULFONAMIDOCHRYSOIDINE® (archaic), SULFACETAMIDE®, SULFADIAZINE®, SULFAMETHIZOLE®, SULFANILIMIDE® (archaic), SULFASALAZINE®, SULFISOXAZOLE®, TRIMETHOPRIM®, TRIMETHOPRIM-SULFAMETHOXAZOLE® (Co-trimoxazole) (TMP-SMX), DEMECLOCYCLINE®, DOXYCYCLINE®, MINOCYCLINE®, OXYTETRACYCLINE®, and Tetracycline.

In methods of treating Diabetes mellitus, including both Type 1 and Type 2 diabetes, or neuropathy of diabetes, the aminosterol composition can be co-administered or combined with drugs commonly prescribed to treat Diabetes mellitus or related symptoms, such as insulin (ular and NPH insulin, or synthetic insulin analogs) (e.g., HUMULIN®, NOVOLIN®) and oral antihyperglycemic drugs. Oral antihyperglycemic drugs include but are not limited to (1) biguanides such as metformin (GLUCOPHAGE®), (2) Sulfonylureas such as acetohexamide, chlorpropamide (DIABINESE®), glimepiride (AMARYL®), Glipizide (GLUCOTROL®), Tolazamide, Tolbutamide, and glyburide (DIABETA®, MICRONASE®), (3) Meglitinides such as repaglinide (PRANDIN®) and nateglinide (STARLIX®), (4) Thiazolidinediones such as rosiglitazone (AVANDIA®) and pioglitazone (ACTOS®), (5) Alpha-glucosidase inhibitors such as acarbose (PRECOSE®) and miglitol (GLYSET®), (6) Dipeptidyl peptidase-4 inhibitors such as Sitagliptin (JANUVIA®), (7) Glucagon-like peptide agonists such as exenatide (BYETTA®), and (8) Amylin analogs such as pramlintide (SYMLIN®).

In methods of treating Parkinson's disease, the aminosterol composition can be co-administered or combined with drugs commonly prescribed to treat Parkinson's disease or related symptoms, such as levodopa (usually combined with a dopa decarboxylase inhibitor or COMT inhibitor), dopamine agonists and MAO-B inhibitors. Exemplary dopa decarboxylase inhibitors are carbidopa and benserazide. Exemplary COMT inhibitors are tolcapone and entacapone. Dopamine agonists include, for example, bromocriptine, pergolide, pramipexole, ropinirole, piribedil, cabergoline, apomorphine, lisuride, and rotigotine. MAO-B inhibitors include, for example, selegiline and rasagiline. Other drugs commonly used to treat Parkinson's disease include, for example, amantadine, anticholinergics, clozapine for psychosis, cholinesterase inhibitors for dementia, and modafinil for daytime sleepiness.

In methods of treating Alzheimer's disease, the aminosterol composition can be co-administered or combined with drugs commonly prescribed to treat Alzheimer's disease or related symptoms, such as Glutamate, Antipsychotic drugs, Huperzine A, acetylcholinesterase inhibitors and NMDA receptor antagonists such as memantine (AKATINOL®, AXURA®, EBIXA®/ABIXA®, MEMOX® and NAMENDA®). Examples of acetylcholinesterase inhibitors are donepezil (ARICEPT®), galantamine (RAZADYNE®), and rivastigmine (EXCELON®).

In methods of treating Huntington's chorea, the aminosterol composition can be co-administered or combined with drugs commonly prescribed to treat Huntington's chorea or related symptoms, such as medications prescribed to help control emotional and movement problems associated with Huntington's chorea. Such medications include, but are not limited to, (1) antipsychotic drugs, such as haloperidol and clonazepam, (2) drugs used to treat dystonia, such as acetylcholine regulating drugs (trihexyphenidyl, benztropine (COGENTIN®), and procyclidine HCl); GABA-regulating drugs (diazepam (VALIUM®), lorazepam (ATIVAN®), clonazepam (KLONOPIN®), and baclofen (LIORESAL®)); dopamine-regulators (levodopa/carbidopa (SINEMET®), bromocriptine (parlodel)), reserpine, tetrabenazine; anticonvulsants (carbamazepine (TEGRETOL®); and Botulinum toxin (BOTOX®); and (3) drugs used to treat depression (fluoxetine, sertraline, and nortriptyline). Other drugs commonly used to treat HD include amantadine, tetrabenazine, Dopamine blockers, and co-enzyme Q10.

In methods of treating peripheral sensory neuropathy, the aminosterol composition can be co-administered or combined with drugs commonly prescribed to treat peripheral sensory neuropathy or related symptoms. Peripheral sensory neuropathy refers to damage to nerves of the peripheral nervous system, which may be caused either by diseases of or trauma to the nerve or the side-effects of systemic illness. Drugs commonly used to treat this condition include, but are not limited to, neurotrophin-3, tricyclic antidepressants (e.g., amitriptyline), antiepileptic therapies (e.g., gabapentin or sodium valproate), synthetic cannabinoids (Nabilone) and inhaled *cannabis*, opiate derivatives, and pregabalin (LYRICA®).

In methods of treating traumatic head and/or spine injury, the aminosterol composition can be co-administered or combined with drugs commonly prescribed to treat traumatic head and/or spine injury or related symptoms, such as analgesics (acetaminophen, NSAIDs, salicylates, and opioid drugs such as morphine and opium) and paralytics.

In methods of treating stroke, the aminosterol composition can be co-administered or combined with drugs commonly prescribed to treat stroke or related symptoms, such as aspirin, clopidogrel, dipyridamole, tissue plasminogen activator (tPA), and anticoagulants (e.g., alteplase, Warfarin, dabigatran).

In methods of treating Amyotrophic lateral sclerosis, the aminosterol composition can be co-administered or combined with drugs commonly prescribed to treat Amyotrophic lateral sclerosis or related symptoms, such as riluzole (RILUTEK®), KNS-760704 (an enantiomer of pramipexole), olesoxime (TRO19622), talampanel, Arimoclomol, medications to help reduce fatigue, ease muscle cramps, control spasticity, reduce excess saliva and phlegm, control pain, depression, sleep disturbances, dysphagia, and constipation.

In methods of treating multiple sclerosis, the aminosterol composition can be co-administered or combined with drugs commonly prescribed to treat multiple sclerosis or related symptoms, such as corticosteroids (e.g., methylprednisolone), plasmapheresis, fingolimod (GILENYA®), interferon beta-1a (AVONEX®, CINNOVEX®, RECIGEN® and REBIF®), interferon beta-1b (BETASERON®, BETAFERON®), glatiramer acetate (COPAXONE®), mitoxantrone, natalizumab (TYSABRI®), alemtuzumab (CAMPATH®), daclizumab (ZENAPAX®), rituximab, dirucotide, BHT-3009, cladribine, dimethyl fumarate, estriol, fingolimod, laquinimod, minocycline, statins, temsirolimus teriflunomide, naltrexone, and vitamin D analogs.

In methods of treating cerebral palsy, the aminosterol composition can be co-administered or combined with drugs commonly prescribed to treat cerebral palsy or related symptoms, such as Botulinum toxin A injections.

In methods of treating epilepsy, the aminosterol composition can be co-administered or combined with drugs commonly prescribed to treat epilepsy or related symptoms, such as anticonvulsants (e.g., carbamazepine (TEGRETOL®), clorazepate (TRANXENE®), clonazepam (KLONOPIN®), ethosuximide (ZARONTIN®), felbamate (FELBATOL®), fosphenytoin (CEREBYX®), gabapentin (NEURONTIN®), lacosamide (VIMPAT®), lamotrigine (LAMICTAL®), levetiracetam (KEPPRA®), oxcarbazepine (TRILEPTAL®), phenobarbital (LUMINAL®), phenytoin (DILANTIN®), pregabalin (LYRICA®), primidone (MYSOLINE®), tiagabine (GABITRIL®), topiramate (TOPAMAX®), valproate semisodium (DEPAKOTE®), valproic acid (DEPAKENE®), and zonisamide (ZONEGRAN®), clobazam (FRISIUM®), vigabatrin (SABRIL®), retigabine, brivaracetam, seletracetam, diazepam (VALIUM®, DIASTAT®), lorazepam (ATIVAN®), paraldehyde (PARAL®), midazolam (VERSED®), pentobarbital (NEMBUTAL®), acetazolamide (DIAMOX®), progesterone, adrenocorticotropic hormone (ACTH, ACTHAR®), various corticotropic steroid hormones (prednisone), and bromide.

In methods of treating depression, the aminosterol composition can be co-administered or combined with drugs commonly prescribed to treat depression, such as any of the class of Tricyclic antidepressants, Monoamine oxidase inhibitors, Selective serotonin reuptake inhibitors, and Serotonin and norepinephrine reuptake inhibitors.

In the methods of treating malignancies, the aminosterol composition can be co-administered or combined with drugs commonly used to treat malignancies. These include all known cancer drugs, such as but not limited to those listed at www(dot)cancer(dot)gov/cancertopics/dru ginfo/alphalist as of May 5, 2014, which is specifically incorporated by reference.

Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second. The regimen selected can be administered concurrently since activation of the aminosterol induced response does not require the systemic absorption of the aminosterol into the bloodstream and thus eliminate concern over the likelihood systemic of drug-drug interactions between the aminosterol and the administered drug.

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLES

Example 1

The purpose of this example was to evaluate the pharmacological effect of squalamine/Aminosterol 1436 administration on gastrointestinal behavior, referred to as "the Aminosterol Induced GI Response."

Gelatin capsules were prepared for oral administration. Capsules were coated in shellac to prevent their release within the stomach. Furthermore, because squalamine and related aminosterols have antibiotic activity, enteric coating prevents the drug from altering the microbial populations of the stomach. The proximal small intestine, where the capsules should dissolve, is normally nearly sterile and hence not significantly perturbed microbiologically by the presence of the aminosterols. Squalamine dilactate powder, 99% pure, or 1436 hydrochloride, 99% pure, was added manually into either Size 0 (for the 200 mg dose) or Size 1 (for the 100 mg dose) gelatin capsules. No excipient was added. The capsules were coated twice in 5% shellac (80% acetone/20% ethanol) and dried before use.

200 mg of squalamine (lactate salt, excipient free) in a coated gelatin capsule was administered orally to a human male in the morning on an empty stomach, with water. Squalamine was synthesized as described in Zasloff et al 2011. Within 2 hours nausea was experienced, lasting about 30 minutes. At 2.5 hours, increased peristalsis ("rumbling gut") was experienced, lasting several minutes. At about 3 hours, a clear watery discharge of about 200 ml was passed rectally. A second episode occurred at 3.2 hours. Following this episode, bowel sounds quieted. No nausea or discomfort was subsequently experienced. Appetite was near normal. Despite normal feeding, feces were not passed for 2.5 days over which time no discomfort was experienced. The first feces passed after this quiescent period was soft and relatively small considering the intake of food and the time interval. Usual bowel functions resumed by about 4 days after squalamine administration.

Results:

Since the normal bowel behavior of this individual is about 1 passage every 24 hours, it can be estimated that 200 mg of squalamine lactate reduced normal small intestinal motility by 2.5 fold. The normal consistency of the stool, despite the delay in passage, reflects a compensatory physiological adjustment in intestinal fluid secretion and absorption, and colonic motility, sufficient to maintain normal moisture content of the fecal material.

Example 2

The purpose of this example was to evaluate the pharmacological effect of squalamine/Aminosterol 1436 administration on gastrointestinal behavior.

200 mg of 1436 (HCl salt, excipients free) in a gelatin capsule was administered orally to a human male in the morning on an empty stomach, with water. Within 1 hour increased peristalsis was experienced, without nausea. At 2 hours, about 100 ml of clear watery diarrhea, recurring at 2.75 hours, 3 hours, 3.25 hours, and 4 hours, with progressively lesser volumes of liquid discharged. First bowel movement was passed at 3.5 days, of normal consistency. The subject experienced no abdominal discomfort, bloating, etc over this period. Usual bowel functions resumed by about 4.5 days after administration of Aminosterol 1436.

Based on this study, it can be estimated that 200 mg of Aminosterol 1436 (HCl salt) has reduced small intestinal motility by 3.5 fold. As noted following the administration of squalamine, the first passed stool was of normal consistency despite the delay in passage.

Example 3

The purpose of this example was to evaluate the pharmacological effect of squalamine/Aminosterol 1436 administration on gastrointestinal behavior.

200 mg of squalamine (lactate salt, excipient free) in a gelatin capsule was administered orally to a human male in the evening following a large meal. No gastrointestinal response related to the administration of squalamine could be perceived either overnight or by the following morning. A normal bowel movement was passed in the morning.

This response suggests that optimal oral dosing should be on an empty stomach. In addition, this observation suggests that squalamine initiates the Aminosterol-Induced GI Response in the proximal small intestine rather than in the distal. Squalamine, because of its physical properties, would be expected to bind tightly to foodstuff, and be unavailable to interact with the intestinal epithelium.

Example 4

The purpose of this example was to evaluate the pharmacological effect of squalamine/Aminosterol 1436 administration on gastrointestinal behavior.

200 mg of squalamine was administered to a human male as in the first example. All stool was collected for 6 days following administration. Stool was then extracted with 60% acetonitrile and 1% HCl overnight. The supernatant was collected and the presence of squalamine assessed by thin layer chromatography following published procedures. Approximately 80% of the dose could be recovered from the stool.

Considering losses and efficiencies of extraction, and known low bioavailability of squalamine in mice and dogs, it can be concluded that the effects observed on the GI tract ultimately resulted from direct interactions between squalamine and gut epithelial and neuronal cells.

Example 5

The purpose of this example was to evaluate the pharmacological effect of squalamine/Aminosterol 1436 administration on gastrointestinal behavior.

100 mg of squalamine was orally administered in a capsule as in the first example. Neither nausea, nor watery diarrhea was experienced. A period of "bowel quiet" was induced, however, that lasted 2 days, after which normally formed feces were passed.

These results teach that the reduction in bowel motility can occur at lower doses of squalamine without the conscious sensation of nausea and the appearance of diarrhea. The soft consistency of the stool, despite its delayed transit time, suggests that luminal fluid exchange in the setting of the Aminosterol-Induced GI Response is physiologically matched to accommodate the reduction in small intestinal motility.

Example 6

The purpose of this Example was to determine whether orally administered squalamine, at a dose sufficient to provoke the complete Aminosterol-Induced GI Response, would stimulate release of GLP-1 into the blood stream.

Enteroendocrine cells, which contain entreric hormones, are known to respond to a variety of stimuli they contact in the intestinal lumen, and release hormones into the submucosa and subsequently into the bloodstream. In particular, GLP-1, the product of the L-cell, is known to have motility effects on the small intestine that resemble those observed after oral administration of squalamine. In this example, a lipid/carbohydrate meal was administered which is known to provoke the release of GLP-1 into the bloodstream. The GLP-1 response of the GI tract to the meal was compared in the presence or absence of squalamine, with blood levels of GLP-1 measured using an ELISA based immunoassay.

The basic protocol was as follows:

Control Response
1. Subject (Caucasian male, 66 yrs, BMI: 2.2, no medical illness) was fasted overnight
2. IV catheter 18 gauge implanted in R decubitus fossa
3. Blood samples drawn at 9:30A, 11A, 11:30A, 12:30 P, 1:30 P, 2 P, 2:30, 3, 3:30, 4:30, 5:30
4. Empty capsule and water at 10:30A
5. Lipid/carbohydrate meal (2 slices of white bread, each with 5.5 gms butter) at 2 P 6. Blood samples: 2 ml into Becton-Dickenson Protease-inhibited Biomarker tubes; 3 ml into standard red top blood collection tubes.
7. All samples were immediately spun at 3000 rpm×15 and serum or plasma aliquotted into 1.5 ml eppendorfs and then stored at −80° C.

Squalamine Response
1. Subject rested 3 days and re-evaluated 4 days after the Control response
2. Fasted overnight
3. IV catheter implanted
4. Samples drawn at 10, 11, 11:30, 12:30, 1:30, 2:30, 3, 3:30, 4:30, 5:30
5. Squalamine capsule, 200 mg at 10:30A
6. Bread and butter, 2 P
7. Blood samlples collected and processed as in the Control study Outcomes:
Squalamine Response: Clinical
Episodes of light headedness 11A-12:15
Episode of mild nausea 1:45
Passage of watery diarrhea: 2 P, 2:20, 2:36, 3:15,
GLP-1 Analyses (Total Immunoreactive GLP-1):
A Millipore ELISA kit was used (Cat #EZGLP1T-36K). A standard curve, provided in the kit, demonstrated linear response between 0->20 pM. The results are shown in Table 1. No significant effect of squalamine on the release of GLP-1 from the small intestine was observed.

TABLE 1

| Control | GLP-1 (pM) | Squalamine | GLP-1 (pM0) |
|---|---|---|---|
| 9:30 | 6 | 10 | 6 |
| 11 | 11 | 11 | 5 |
| 11:30 | 12 | 11:30 | 4 |
| 12:30 | 17 | 12:30 | 10 |
| 1:30 | 7 | 1:30 | 9 |
| 2:30 | 11 | 2:30 | 8 |
| 3:00 | 12 | 3:00 | 8 |
| 3:30 | 1 | 3:30 | 6 |
| 4:30 | 5 | 4:30 | 5 |
| 5:30 | 10 | 5:30 | 3 |

This Example demonstrates that orally administered squalamine does not pharmacologically stimulate secretion of Enteroendocrine cells expressing GLP-1, and that the effects on bowel motility cannot be a consequence secondary to the presence of elevated levels of GLP-1.

Example 7

The purpose of this example was to evaluate the effects of squalamine, orally dosed, on Irritable Bowel Syndrome (IBS).

A 66 year old female, in otherwise good health, was suffering from the "mixed" form of IBS since early childhood. The condition was characterized by a failure to feel "cleared" after the passage of a stool; occasional crampiness; abdominal bloating and a sense of "fullness." The condition caused her to be "conscious of her bowels" throughout the day, and frequently interrupted her sleep. Attempts to relieve herself on the toilet would generally be ineffective, leaving her with the feeling of "still having to go."

On day 1 the individual was administered a single 200 mg capsule of squalamine, orally, on an empty stomach with water. Within 2 hrs she experienced nausea, at 3 hrs she vomited, followed soon after by the passage of about 200 ml of clear discharge rectally. By 3.5 hrs the nausea had passed. She ate normally at lunch and dinner. She experienced "bowel quiet" from Day 1 through Day 5 on a single dosing, without cramping or urgency. Slept better than she had in many years. The first stool was passed on Day 4, was soft and passed easily, and then successively on Days 5, 6, 7, and 8. Beginning at Day 6, she began to experience the prior GI symptoms. By Day 8, her usual GI symptoms had returned.

A second dosing trial was begun on Day 15, with a 50 mg capsule administered. Neither nausea nor a discharge was experienced. Sense of bowel quiet was experienced. Bowel movement was passed on Day 17. A 25 mg capsule was administered on Day 19. By Day 21 the previous symptoms of IBS were returning. It was assumed that 50 mg dosed every other day was an optimum regimen. The individual remained on a dosing schedule of 50 mg orally every other day.

At 10 months of dosing the individual no longer experiences symptoms of IBS. Bowel movements are of normal consistency. Sleep is no longer interrupted by urgency to defecate. Individual believes that the treatment has resulted in improvement of mood and responsible for a "sense of well-being." Stools are somewhat smaller than previously noted, and passed generally once daily.

This Example demonstrates the utility of the invention for the treatment of Irritable Bowel Syndrome and establishes an effective dosing regimen.

Example 8

The purpose of this example was to evaluate the effects of squalamine, orally dosed, on the constipation associated with Parkinson's disease.

A 70 yr old male, in otherwise good health, presented with Parkinson's disease of about 5 yrs duration. He was severely constipated and suffered from frequent episodes of cramping. These GI symptoms were similar to that described in Parkinson's and could not be alleviated medically or through dietary adjustment. His medications included 5 L-DOPA/DDC caps/day and 1-2 Requip before bedtime. His neurological status at this time was as follows, as determined about 1 hour after an L-DOPA dosing, a time point when he appears to be repleted with dopamine:

Slow walking with shuffling . . . need to squat intermittently
Articulation poor . . . difficult to understand his speech . . . halting
Use of utensils while eating involved slow, awkward movements
Face seemed a bit mask like; unconsciously made chewing movements
Cognitive function (memory, wit) was less than observed 3 months prior
Balance was unsteady
Mood was depressed
Swallowing noted to be difficult at times
Chewing food was slow
Handwriting was small Began oral dosing with 200 mg capsule of squalamine on Day 1. Capsule was taken in the AM before breakfast, along with L-DOPA. No nausea experienced nor watery discharge. Passed several moist stools on Day 1. 200 mg cap on day 2 provoked a watery diarrhea at 2 hrs after dosing, but discharge subsided by day 3 dosing. On day 13, subsequent dosing was maintained at 200 mg every other day, with some minor degree of nausea. No watery discharge. At about Day 30 the subject was switched to 100 mg every other day, and remained on this regimen for about 9.5 months.

The therapeutic response to administration of squalamine was progressive and objectively apparent, as detailed in Table 2

TABLE 2

| Time Point | Observations |
| --- | --- |
| 3 Weeks (Observations were collected over 3 days) | Bowels improved considerably<br>Walking more comfortably, but still uneven<br>Subject feels breathing is easier<br>Articulation much improved<br>Able to touch the back of front upper teeth with his tongue<br>Mood seems to have improved<br>Some shaking even after L-DOPA<br>Balance still poor in the AM, but some improvement observed |
| 2 Months (Observations were collected over 5 days) | Normal bowel functions; no constipation; no GI issues; no cramping<br>No shaking of arms and legs<br>Walking more smoothly, arms swinging more naturally<br>Increased stamina<br>Subject could hold various objects in his hand while walking a block or two or walking up stairs; unlike previously, now appeared confident in being able to hold objects while he walked<br>Could sustain concentrated work which involved sorting through papers, bending over to pick up and move papers; he did this for 2.5 hours without stopping. Until now his ability to sustain this moving and bending was very limited such that he reported pain in his back and general weakness that shortened the work sessions to less than one hour.<br>Subject's ability to handle utensils when he eats was much improved; he could control the fork and spoon in a natural way which was not the case a few months ago. The speed of his ability to move the utensils was very normal looking now as opposed to the very slow pace at which he moved utensils over the past months.<br>Subject still reports periods when he feels very tired. However over the 5 days of observation as opposed to the previous visit, he did not need to squat down to relieve his legs from feeling exhausted.<br>He walked without shuffling<br>His speech is now smooth and normal in volume and articulation. This was not the case months ago. He did not report having difficulty swallowing now, as opposed to before. He was able to talk and eat at the same time.<br>He has retained an oral mannerism in which he chews his tongue/cheek. This has developed over the past few months. He is aware that he is doing it and reports it has become a habit.<br>Subject did not make any extreme mannerisms of the face that had begun to be seen over the past few months<br>Subject has expressed hopefulness regarding the regaining of strength and a general feeling of better health. This hopefulness is new.<br>Though historically an anxious personality, Subject seems less so now. Seems more capable of controlling anxiety and making positive decisions: moving out of his office, packing, disposing of unnecessary property, papers, etc.<br>The most evident Parkinson's disease sign that remained was instability when being pushed or pulled. He would lose balance and compensate by moving in the direction of the force with faltering choppy steps, along with vocalizing "Oh, Oh, Oh . . ."<br>Medication needs remained stable. |
| 9 months (Observations were collected over 5 days) | Bowel functions normal<br>Generally, within about an hour after taking an L-DOPA dose, Subject does not have the appearance or behavior, or signs of a person with Parkinson's disease.<br>Balance, as tested in the previous visit, by push or pull was met with resistance on his part, opposing applied force. Subject remained upright and stable, not moving from his standing position.<br>All movements (hands, walking,) are all smooth and normal.<br>No shaking noted<br>Walking is strong without any evidence of shuffling.<br>Was able to walk on even terrain in the course of a hike through Will Rogers Park, lasting about 2 hours. Was then eager to continue on through a visit to the Getty Museum. No fatigue.<br>Excellent stamina.<br>Mood has been upbeat<br>Articulation normal<br>Handwriting seems normal<br>Cognitive functions normal. Memory normal.<br>Medication needs have remained stable: 4 L-DOPA, + 1-2 Requip/day. |

This Example suggests that orally administered squalamine has therapeutic benefit in Parkinson's disease and establishes an effective dosing regimen. The assessment is that there appears to be 2 potential targets. The first is the dopamine producing cells within the substantia nigra. The second is the functionality of the nervous system circuitry. Squalamine appears to have restored function to the nervous system, permitting near normal functioning when the subject is replete with dopamine (administered exogeneously). The aminosterol dosing regimen may possibly have stopped further deterioration of the dopamine producing tissues, or perhaps even restored some addition production capacity, but if so this effect is much less apparent than the recovery of overall neurological behavior.

The progression of nervous system recovery appears to begin with the GI tract, the target being affected most likely the enteric nervous system. Constipation resolved within several weeks. A bit later, improvement in articulation was noticed. Arm and leg movement follow. Last to improve is balance.

Example 9

The purpose of this example was to evaluate the effects of squalamine, orally dosed, on the neurological signs associated with Parkinson's disease in an individual without the usual Parkinson's associated constipation and GI disorders and likely a "Parkinson's-like" syndrome.

The individual was a male, 59 years old. He was a psychiatrist specializing in addiction. Movement disorder began at age 53. Original diagnosis was multiple sclerosis. Presenting symptoms were depression and difficulty in controlling the action of sitting in chair. He would "plop" onto a sit without braking the movement. An MRI showed many diffuse lesions scattered throughout the cortex, which appear to have remained stable. Treatment with L-DOPA caused some correction of the sitting difficulty, leading to the presumptive diagnosis of Parkinson's disease. Therapy continued with increasing doses of Sinemet, followed by addition of ropinirole. Deterioration continued (despite an L-DOPA dose exceeding 10-11 pills/day), ropinirole (5×2 mg and 4×1 mg, daily) and amantadine was added. He was on Wellbutryn for depression. There had been no history of GI disorders, and bowel function was said to be normal.

The individual lived at home with a wife and 2 children. He had to be driven to work. Walking was unsteady. His speech was nearly incomprehensible. Face was mask-like. No obvious tremors. Walking was hesitant. Subject had fallen (or tripped) several times previously and used a cane. Table 3 summarizes the dosing protocol and observations.

TABLE 3

| Timing | Observations |
|---|---|
| Day 1 | Subject took a 100 mg cap of squalamine. No obvious GI response. Continued on 100 mg every other day. |
| Day 9 | Observed Subject walking smoothly and briskly from a distance without walker or cane. |
| Day 14 | Subject sounded more coherent than previously. This was noted, as well by his patients. |
| Day 21 | Individual independently began 200 mg every other day. Others noted that his articulation had become noticeably better. His self-confidence was noted to be improving and his energy level was increasing. |
| Month 3 | Subject ran out of squalamine 2 weeks prior. Cessation was followed by "the worst constipation he had ever remembered." This resolved spontaneously over the following few days. He also noted that he "was not feeling as good" as when on it . . ." not exactly depression..hard to explain . . ." His articulation was clear. |
| Month 4 | Subject began 100 mg every other day. Discovered that his family situation was extremely unstable and he was anticipating a divorce or separation. He stopped taking L-DOPA on a regular basis but continued on squalamine. |
| Month 5 | Subject independently raised dose to 200 mg every day at month 5.5. No GI issues (i.e., diarrhea). Commented that colleagues noted improvement. Took several falls which he attributed to "risky behavior" on his part. |
| Month 6 | Individual could compensate being pulled and pushed without faltering. He told me that he felt his balance had improved. Still had difficulty initiating walking. No tremor. Voice was of low volume. Face was still mask-like. Once moving subject walked without shuffling. Subject was still having very complex family issues. Steadfastly insisted on continuing squalamine. Medication dosing had not changed. |

This Example suggests that squalamine can provide therapeutic benefit in individuals with a Parkinson's like syndrome in whom no initial gastrointestinal symptoms are noted.

Example 10

An experiment was conducted in the mouse to test the hypothesis that squalamine was acting on the enteric nervous system, as predicted by the clinical responses observed in human subjects.

Figure 1B:
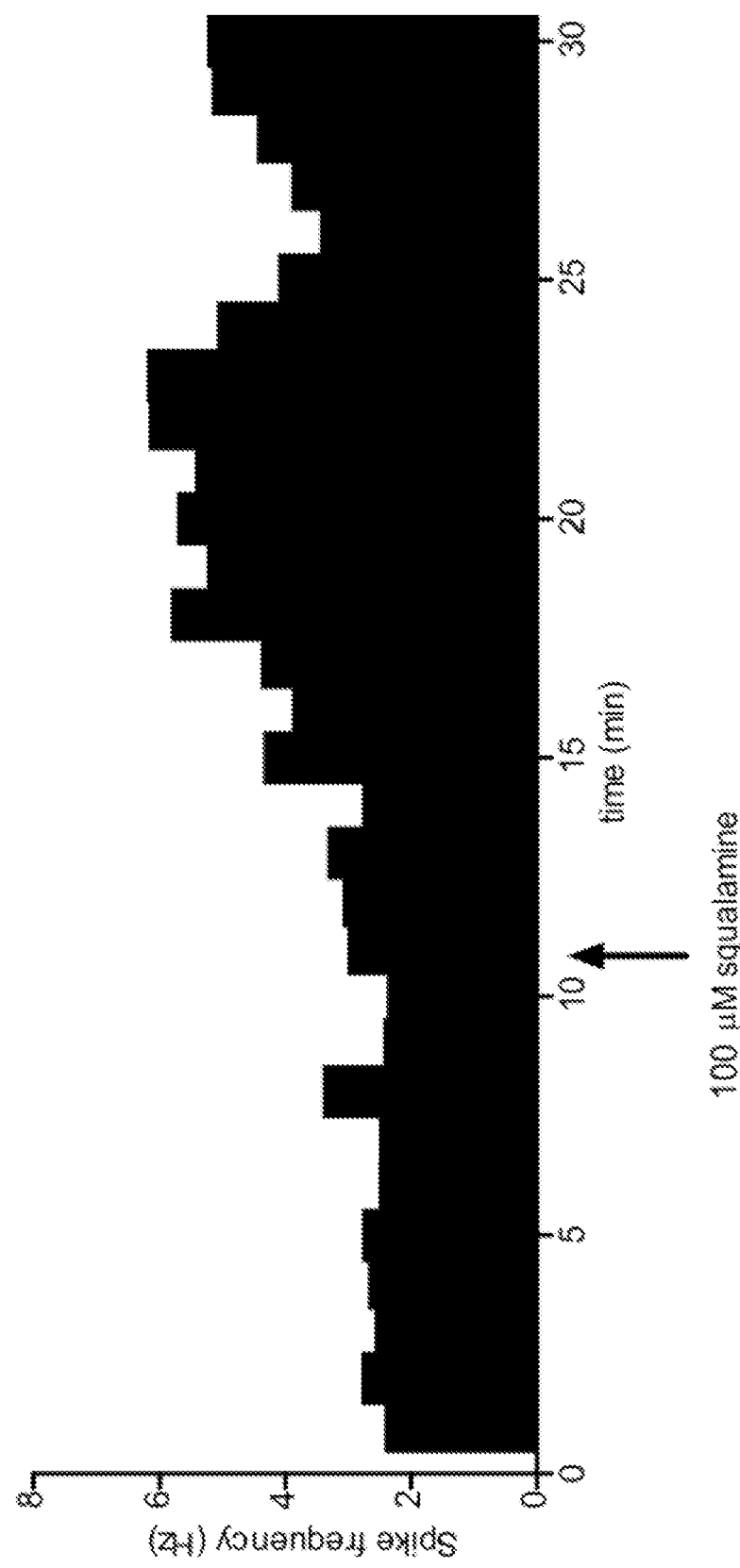
FIG. 1B shows a histogram of multiunit firing frequency averaged over 1 min bins. Squalamine was applied into the lumen by gravity feed 11 min after beginning the recording.

Under appropriate and approved anesthesia, the distal colon of a mouse was externalized from the abdomen, along with the mesentary. The mesenteric blood vessels and lymphatics were carefully dissected from the mesenteric nerve, a structure that contains both the vagus (efferent and afferent) and spinal afferents. The nerve was cut, and the free end (which receives signals from the gut) was introduced into a capillary housing a silver electrode, along with the appropriate electronics required to detect and amplify weak electrical signals pulsing from the gut through the mesenteric nerve. As seen in FIG. 1, introduction of squalamine into the lumen of the colon results in an increase in electrical activity directed toward the brain from the gut nervous system. Concentrations of 3, 10, 30 and 100 µM squalamine were evaluated. Responses to squalamine application were discernible at 30 µM but robust and reproducible responses were first evident at 100 µM. At the latter concentration, 5 experiments were successfully performed and each revealed that squalamine evoked an increase in the mesenteric nerve multiunit firing frequency. Paired experiments were comparisons of average discharge rates of a control recording period with a three-minute period during the peak response to squalamine. Statistical comparisons were made using paired t-tests. Squalamine increased the background firing rate from (mean±SD) 2.0±1.2 to 5.2±3.1 Hz (P=0.03). The latency to the onset of the firing increase was 4.4±4.1 min, while the latency to peak of the firing rate increase 12±7.5 min (FIG. 1).

This Example teaches that squalamine, administered to the gut lumen, stimulates enteric neurons, and that some of these neurons can send currents to centers in the CNS. This supports the utility of orally administered squalamine in those conditions in which stimulation of afferent currents within the vagus could provide therapeutic benefit.

Example 11

An experiment was performed to determine the effect of squalamine on colonic motility and intraluminal pressure.

Figure 2A:
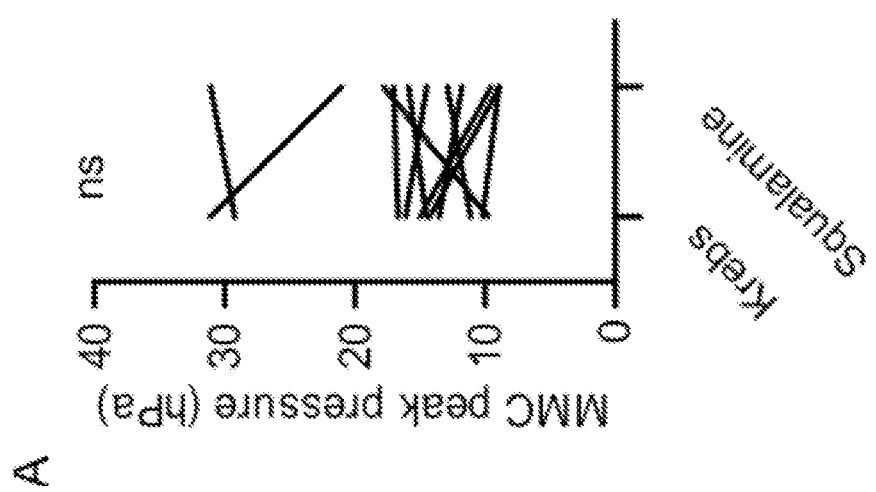
FIG. 2A shows that intraluminal application of squalamine had no apparent effect on mouse colon migrating motor complex (MMC) peak pressure waves, although
Figure 2B:
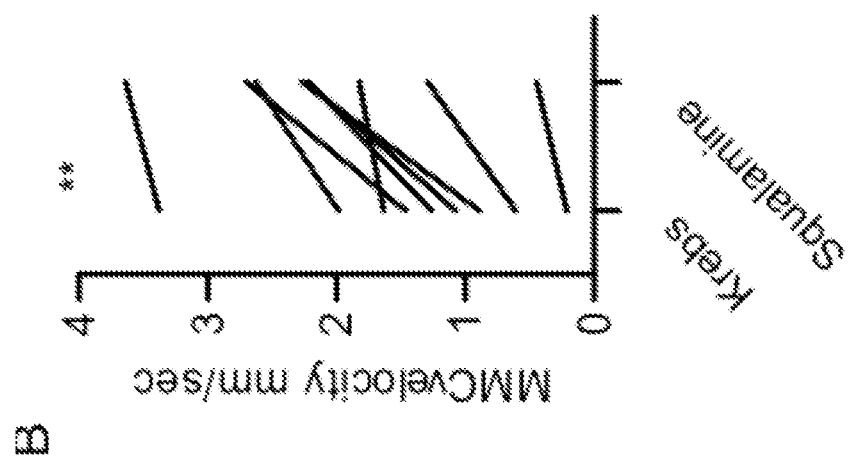
FIG. 2B shows that MMC propagation velocity from oral to anal was increased.

A segment of colon was excised from a mouse, and one end was attached to a glass tube housing a pressure sensor. A video camera recorded the visible contractions of the segment. When squalamine was added to the colonic lumen, the frequency of contractions increased about 2 fold, representing coordinated peristaltic waves that move toward the rectum. The peak pressure of these waves did not differ from those observed prior to squalamine application. The data are shown in FIG. 2.

This Example demonstrates that squalamine has "anti-constipation" properties. This animal model is used to demonstrate, for example, the constipation inducing properties of opioid, such as loperamide. This Example supports the utility of squalamine in human disorders characterized by delayed colonic motility.

Example 12

An experiment was conducted in the mouse to determine whether squalamine can stimulate the instrinsic primary afferent neurons (IPANs) of the colon, the neurons that act within the colon to influence motility and secretion.

Figure 3:
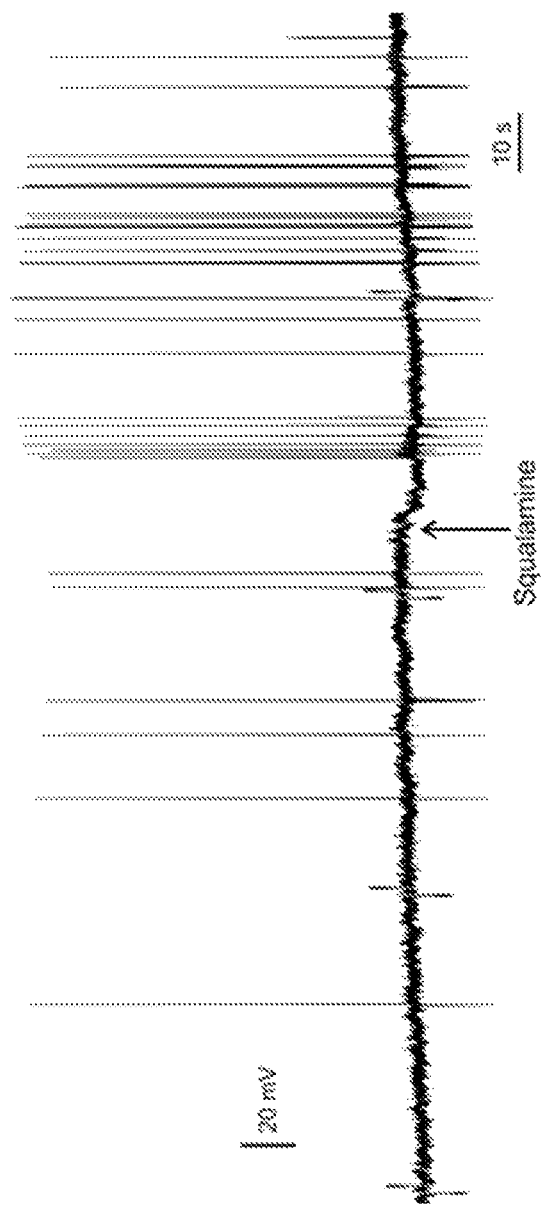
FIG. 3 shows a representative recording of IPAN member potential. Squalamine evoked bursts of action potential lasting for 10 to 30 min after application of a brief (20 ms) 50 L puff of squalamine onto the epithelium.

In this experiment the outer adventitial layer of the mouse colon is peeled away exposing the IPANs. Individual IPANs within the myenteric plexus of the wall of the colon are patched using a patch-clamp apparatus. These cells represent the major neuronal population that communicate sensory data from the gut. They synapse with the various nerve networks within the gut that influence muscle and secretory activity, as well as connecting with vagal nerve endings. Administration of squalamine at 30 µM to the lumen (applied via a 50 ms "puff" of solution) leads to a very sustained (10 min) burst of electrical activity (FIG. 3).

This Example shows that the nerve ending of these key sensory cells, which lie near the luminal surface of the colon, can detect squalamine and respond electrically with robust, long lived signals. Moreover, this Example shows that squalamine's effect on intestinal motility and muscle contraction (and possibly secretion) are likely a consequence secondary to stimulation of the IPANs, which in turn communicate to the myenteric and submucosal plexus.

Example 13

An experiment was conducted to determine whether squalamine stimulated the IPANs directly or indirectly.

In this Example the same procedure as that described in Example 12 was followed except that the epithelial lining of the colon was peeled away prior to application of squalamine to the lumen. Signals from individual IPANs were recorded. Concentrations of squalamine as low as 1 uM could now stimulate a robust response, similar quantitatively (and qualitatively) to concentrations 30-100 fold higher, when an intact epithelium was present.

This Example clearly shows that squalamine interacts directly with the neurons of the intestine to stimulate activity. If the compound acted indirectly on the nervous system, i.e., by stimulating enterochromaffin cells to release neutrotransmitters such as serotonin or histamine, which, in turn, stimulated their receptors on the nerve cells, stripping of the epithelium would have caused the opposite result, namely the loss of squalamine responsiveness. This Example supports the utility of squalamine in the treatment of diseases of the nervous system where reduction in the net surface potential of the intracellular membrane could elicit benefit, such as in the displacement of alpha-synuclein from the plasma membrane of neurons in Parkinson's disease.

Example 14

The purpose of this Example was to demonstrate the capacity of squalamine to displace alpha-synuclein from membranes that exhibit a negative surface potential.

Alpha-synuclein was mixed with a preparation of vesicles consisting of DOPE (50%), DOPS (30%), DOPC (20%). The concentration of lipid was 2.4 mM; the concentration of N-terminally acetylated alpha-synuclein was 10 µM. The interaction was followed by circular dichoroism. The concentration of squalamine was increased in 40 µM increments. As the concentration of squalamine increased, a linear decrease in the amount of alpha-synuclein membrane bound was observed, reflecting the higher affinity of squalamine than alpha synuclein for the negatively charged phospholipids. At a ratio of lipid to squalamine of 15:1, full displacement of alpha-synuclein was observed. Addition of squalamine to a solution of alpha-synuclein alone had no effect on the circular dichroism spectrum.

This Example demonstrates that squalamine has the capacity to physically reduce the concentration of membrane bound alpha-synuclein. Hence, this Example supports the utility of administering squalamine and related aminosterols in conditions where alpha-synuclein/membrane interactions are believed to cause pathology, such as in Parkinson's disease. Beta-Amyloid, the protein associated with Alzheimer's, like alpha synuclein, is known to bind to anionic phospholipids; from the results of this Example, it would be logical to assume that squalamine and other related aminosterols should displace Beta-amyloid from its target membranes, supporting its utility in the treatment of Alzheimer's disease.

Example 15

An experiment was conducted to determine whether squalamine exhibited efficacy in the treatment of Opioid induced constipation.

A normal subject began dosing with 1 tab codeine 30 mg/acetaminophen 300 mg at 8 A on Day 1, and repeated on Day 2 and Day 3. Normal bowel movement frequency was 1 or more stools/day, normally formed. Prior to codeine on Day 1, subject passed a normal stool in the AM. No bowel movements from the start of dosing through the 8A Day 3 dose. No cramping; some gas. Some sense of fullness on the evening of Day 2.

At 9:15A subject was administered 200 mg cap of squalamine. Within about 10 min the subject had a cup of coffee and some cookies. No nausea. No clear rectal fluid. At 11:15A, the subject passed a large soft, well formed stool with normal urgency. A second smaller stool was passed at 12:30. A third, large watery stool was passed at 7 P. A sense of bowel relief was appreciated by the subject. The rapid effect on colonic motility seems unlikely to have been a direct effect of squalamine on the colon, but perhaps a downstream consequence of enteric nervous system stimulation. On Day 4, 30 mg codeine. No squalamine dosing. 7 P passed a loose stool of normal volume.

This Example suggests that the Aminosterol-Induced GI Response can over-ride the inhibitory effects of opioids on GI function. Moreover, this Example provides evidence that squalamine and related aminosterols can exert therapeutic benefit in the setting of opioid-induced constipation.

Example 14

The purpose of this example was to demonstrate the utility of stimulating the Aminosterol-Induced GI Response to induce compete regression in untreatable, unresectable Stage 4b colon cancer.

A 65 year old white male presented with abdominal distention, pain, and progressive weight loss of several months duration. Radiographic studies revealed widely disseminated masses throughout the abdomen. An exploratory surgical procedure revealed widespread implants of a mucinous adenocarcinoma, throughout the peritoneum, on and within the liver, and covering the other major organs without a clear primary tumor. Because of the extent of the cancer, the decision to close was made and no further treatment other than symptomatic management and end of life care was suggested.

The individual was begun on a total daily dose of 50 mg of squalamine, administered as 25 mg twice daily, as a powder dispersed in apple sauce. Approximately 6 months after initiation of squalamine treatment the individual was seen again at the hospital due to the chance recognition of a mass on his right kidney. The kidney was surgically removed, and during the procedure the peritoneum explored. No tumor was visible. The mass on the kidney was a benign cyst. Treatment with squalamine continued daily for 5 years. The individual had no recurrence of cancer. The subject died at age 83 of a myocardial infarction.

Example 15

The purpose of this example was to demonstrate the utility of stimulating the Aminosterol-Induced GI Response to induce regression of endometrial cancer.

A 66 year old white female presented with abdominal discomfort and the presence of a palpable abdominal mass. Radiographic studies revealed the presence of a uterine mass and numerous affected nodes extending from supraclavicular to peritoneal. Surgical removal of the uterus and ovaries was followed by chemotherapy. Subsequently, a large tumor adherent to the distal colon was discovered, along with additional nodes. A colonic resection was performed along with local radiation to the peritoneum.

The individual decided to stop all chemotherapy due to progression of the cancer and the adverse reactions previously experienced. The subject began oral squalamine in capsule form in August 2012. By March 2013, no evidence of malignancy was visible by PET/CT imaging. In July 2013 a small tumor appeared adjacent to the right ureter, and a second attached to the left descending colon. The dose of squalalmine was raised to 100 mg/day in two divided doses. In October 2013, the tumor adjacent to the ureter was irradiated. In February 2013, the small mass adherent to the colon remained active by PET/CT, slightly larger than when first noted in July 2013, and no additional metastases were observed. The individual remains on squalamine 100 mg/day. She is in otherwise excellent health.

Example 16

The purpose of this example was to demonstrate the utility of stimulating the Aminosterol-Induced GI Response to induce regression of Stage 4b pancreatic cancer A 67 year old white female presented with abdominal discomfort, weight loss, and malaise. After considerable medical consultations a diagnosis of pancreatic adenocarcinoma was made. The subject was treated with chemotherapy and experienced a severe adverse reaction, which included ascites and pleural effusion. In July 2013, a PET/CT revealed the presence of a mass in the head and tail of the pancreas along with several tumors in the liver and numerous active peripheral lymph nodes. In August 2013, the subject was evaluated for a clinical trial at TGEN in Arizona, but not admitted due to the extensive cancer evident in the pancreas, liver, and nodes.

In late August 2013, the subject was begun on 50 mg/day, then increased to 100 mg/day after a week. The subject began once monthly cycles of cisplatin and 5-FU. A PET/CT scan in early December 2013 revealed the dramatic reduction in PET intensity of all previously active cancer. A PET/CT scan of February 2014 revealed the complete loss of all PET active masses, including the lymph nodes. The overall level of performance of the individual continues to improve, but the ascites and pleural effusions persist. Cytology of the peritoneal fluid remains negative for abnormal cells. All concurrent chemotherapy has stopped. Squalamine treatment continues.

Example 17

The purpose of this example was to demonstrate the utility of stimulating the AIR to induce regression of a brain tumor.

A 63 year old white male presented with headache and memory loss. Radiographic studies revealed the presence of large stellate gliobastoma. The tumor was partially resected surgically, followed by local radiation. The subject was placed on a clinical protocol evaluating everolimus and temozolimide.

In mid October 2013, the subject began squalamine capsules with a 100 mg single dose. In early December 2013, an MRI revealed that the tumor mass had decreased by about 20%, and a second study in the beginning of February 2014 revealed continued shrinkage of the residual tumor to 60% of its volume after the surgery/radiation. Squalamine treatment continues.

Example 18

The purpose of this example was to demonstrate the utility of stimulating the Aminosterol-Induced GI Response to induce repression of lymphoma.

A 92 year old white female with a 2 year history of progressive dementia and weakness presented with a massive cervical, axillary, and inguinal lymphadenopathy, along with malaise, somnolence and pain. Clinical chemistries revealed mild hypercalcemia, increased polyclonal immunoglobulins, and no abnormal cells in the blood. An MRI of the cervical area revealed massive adenopathy, with several nodes as large as walnuts. The skin of her feet was a nonblanching bright pink hue up to the ankle with a scattered brownish purpuric rash. The individual was provided end of life care.

At the end of December 2013, the individual was begun on a daily dose of one 50 mg capsule of squalamine. Previously constipated, bowels began to move. Rash cleared within 3 days. On day 4 after squalamine initiation, a short course of dexamethsone was begun to treat the hypercalcemia, and stimulate appetite. 20 mg (4 days), 16 mg (2 days), 8 mg, 4 mg (2 days), then 2 mg daily. By 1 week a marked reduction in the size of the nodes was noted. Mid-January 2014 weakness on the right, involving arm and leg was noted; a diagnosis of a mild stroke was made. Physical examination at the end of February 2014 revealed no palpable cervical nodes. A flat left submandibular node was felt of normal size and consistency. A repeat clinical chemistry study demonstrated complete resolution of the polyclonal gammopathy and return to normal serum values. Squalamine treatment continues.

Example 19

The purpose of this example was to demonstrate the utility of stimulating the Aminosterol-Induced GI Response to induce regression of a sarcoma and the method by which dosing is arrived at.

A 22 year old man was seen because of the recurrence of an embryonal rhabdomyosarcoma. At age 20 he noticed a mass in his left groin. An MRI revealed a soft tissue mass; and a biospsy revealed the mass to be a spindle cell embryonal rhabdomyosarcoma. The mass was surgically excised. The patient was then treated with a cocktail of chemotherapeutic agents. Several konths later the mass was seen to recur in the left groin. The mass was again excised. Several months later, a tumor was gain noted in the groin, with a large mass present in the left lung.

The patient was begun on 100 mg capsules of squalamine for several days, without any noticeable GI symptoms. The dose was raised to 200 mg daily, again without any GI response. At 300 mg daily, a clear effect was noted, that being mild nausea, 2 hours after dosing, followed by a bowel movement later in the day. 3 weeks after initiation of dosing the lung tumor was removed surgically and exhibited a massive internal hemorrhage due to blood vessel damage; dosing continued. 2 months post surgery there was no evidence of pulmonary tumors nor evidence of recurrence of any soft tissue tumor in the groin.

It will be apparent to those skilled in the art that various modifications and variations can be made in the methods and compositions of the present invention without departing from the spirit or scope of the invention. Thus, it is intended that the present invention cover the modifications and variations of this invention, provided they come within the scope of the appended claims and their equivalents.

REFERENCES

Ahima et al., "Appetite suppression and weight reduction by a centrally active aminosterol." *Diabetes*, 51(7): 2099-104 (2002).

Akhter et al., "Squalamine, a novel cationic steroid, specifically inhibits the brush-border Na+/H+ exchanger isoform NHE3." *Am. J. Physiol.*, 276(1 Pt 1): C136-44 (1999).

Alexander et al., "Membrane surface charge dictates the structure and function of the epithelial na+/h+ exchanger. EMBO J., 30:679-691(2011)

Bhargava et al., "A phase I and pharmacokinetic study of squalamine, a novel antiangiogenic agent, in patients with advanced cancers," *Clin. Cancer Res.*, 7(12): 3912-9 (2001).

Delgado et al., "Neuroprotective effect of vasoactive intestinal peptide (VIP) in a mouse model of Parkinson's disease by blocking microglial activation." *Faseb. J.*, 17(8): 944-6 (2003).

Genaidy et al., "Effect of squalamine on iris neovascularization in monkeys." *Retina*, 22(6): 772-8 (2002).

Gonzalez-Rey et al., "Therapeutic effect of vasoactive intestinal peptide on experimental autoimmune encephalomyelitis: down-regulation of inflammatory and autoimmune responses," *Am. J Pathol.*, 168(4): 1179-88 (2006)

Gressens et al., "Vasoactive intestinal peptide prevents excitotoxic cell death in the murine developing brain," *J. Clin. Invest.*, 100(2): 390-7 (1997).

Hao et al., "A Phase I and pharmacokinetic study of squalamine, an aminosterol angiogenesis inhibitor," *Clin. Cancer Res.*, 9(7): 2465-71 (2003).

Herbst et al., "A phase I/IIA trial of continuous five-day infusion of squalamine lactate (MSI-1256F) plus carboplatin and paclitaxel in patients with advanced non-small cell lung cancer," *Clin. Cancer Res.*, 9(11): 4108-15 (2003).

Higgins et al., "Squalamine improves retinal neovascularization," *Invest. Ophthalmol. Vis. Sci.*, 41(6): 1507-12 (2000).

Higgins et al., "Regression of retinopathy by squalamine in a mouse model," *Pediatr. Res.*, 56(1): 144-9 (2004).

Li et al., "Squalamine and cisplatin block angiogenesis and growth of human ovarian cancer cells with or without HER-2 gene overexpression," *Oncogene*, 21(18): 2805-14 (2002).

Li et al., "GLP-1 receptor stimulation preserves primary cortical and dopaminergic neurons in cellular and rodent models of stroke and Parkinsonism," *Proc. Natl. Acad. Sci. USA*, 106(4): 1285-90 (2009).

MacDonald, D. (1995). "Squalamine for STDs." Abstract no F7 35th ICAAC conference.

Moore et al., "Squalamine: an aminosterol antibiotic from the shark," *Proc. Natl. Acad. Sci. USA*, 90(4): 1354-8 (1993).

Rao et al., "Aminosterols from the dogfish shark *Squalus acanthias*," *J. Nat. Prod.*, 63(5): 631-5 (2000).

Salmi et al., "New stereoselective titanium reductive amination synthesis of 3-amino and polyaminosterol derivatives possessing antimicrobial activities," *Eur. J. Med. Chem.*, 43(3): 540-7 (2008).

Salmi et al., "Squalamine: an appropriate strategy against the emergence of multidrug resistant gram-negative bacteria?" *PLoS ONE*, 3(7): e2765 (2008).

Schiller, J. H. and G. Bittner, "Potentiation of platinum antitumor effects in human lung tumor xenografts by the angiogenesis inhibitor squalamine: effects on tumor neovascularization," *Clin. Cancer Res.*, 5(12): 4287-94 (1999).

Selinsky et al., "Squalamine is not a proton ionophore," *Biochim. Biophys. Acta.*, 1464(1): 135-41 (2000).

Selinsky et al., "The aminosterol antibiotic squalamine permeabilizes large unilamellar phospholipid vesicles," *Biochim. Biophys. Acta.*, 1370(2): 218-34 (1998).

Sills et al., "Squalamine inhibits angiogenesis and solid tumor growth in vivo and perturbs embryonic vasculature," *Cancer Res.*, 58(13): 2784-92 (1998).

Sokoloff et al., "Adjunctive therapy for men with high risk localized and locally advanced prostate cancer: targeting disseminated tumor cells," *J. Urol.*, 172(6 Pt 2): 2539-44 (2004).

Steinberg, B. E. and S. Grinstein, "Pathogen destruction versus intracellular survival: the role of lipids as phagosomal fate determinants," *J. Clin. Invest.*, 118(6): 2002-11 (2008).

Sumioka et al., "TARP phosphorylation regulates synaptic AMPA receptors through lipid bilayers," *Neuron*, 66(5): 755-67 (2009).

Tirassa et al., "CCK-8 prevents the development of kindling and regulates the GABA and NPY expression in the hippocampus of pentylenetetrazole (PTZ)-treated adult rats," *Neuropharmacology*, 48(5): 732-42 (2005).

US 2005/0261508A1 for "Aminosterol Compounds useful as inhibitors of the sodium/proton exchanger (NHE), pharmaceutical methods, and compositions employing such inhibitors, and processes for evaluating the NHE-inhibtory efficacy of compounds," Zasloff et al., Published 11/24/05.

US 2006/0166950A1 for "Treatment of neovascularization disorders with squalamine," Zasloff et al., Published Jun. 27, 2006

US 2006/0183928A1 for "Aminosterol Compounds useful as inhibitors of the sodium/proton exchanger (NHE), pharmaceutical methods, and compositions employing such inhibitors, and processes for evaluating the NHE-inhibtory efficacy of compounds", Published Aug. 17, 2006

US 2007/10504A1 for "Polymorphic and Amorphous salt forms of squalamine dilactate" Chellquist, Doubleday, Gilbert, Zhang, McLane, Armbruster, Levitt, Published Jan. 11, 2007

US 2011/0097303 for "Methods and Compositions for Treating and Preventing Viral Infections," published Apr. 28, 2011, Zasloff U.S. Pat. No. 5,192,756 for "Aminosterol antibiotic," Zasloff, Moore, Wehrli, Issued Mar. 9, 1993

U.S. Pat. No. 5,637,691 (1993) for "Steroid derivatives, pharmaceutical compositions containing them, and their use as antibiotics and disinfectants", Frye, Zasloff, Kinney, Moriarty.

U.S. Pat. No. 5,721,226 (1998) for "Methods for treating angiogenesis using squalamine and squalamine steroid derivatives," Frye, Zasloff, Kinney, Moriarty, Collins U.S. Pat. No. 5,733,899 (1998) for "Methods for treating infections using steroid based pharmaceutical compositions," Frye, Zasloff, Kinney, Moriarty, Collins U.S. Pat. No. 5,763,430 (1998) for "Method of treating a viral infection by administering a steroid compound," Zasloff.

U.S. Pat. No. 5,792,635 (1998) for "Method of inhibiting the sodium-proton exchanger NHE3 and method of inhibiting growth by administering squalamine," Zasloff.

U.S. Pat. No. 5,795,885 (1998) for "Method of Inhibiting proliferation of cells by administering an aminosterol compound," Zasloff, Shinnar, Kinney, Anderson, Williams, McLane.

U.S. Pat. No. 5,834,453 (1998) for "Methods for the manufacture and use of antimicrobial sterol conjugates," Regen (Leheigh Univ).

U.S. Pat. No. 5,840,740 (1998) for "Aminosterol compounds and a method of treating infection using the aminosterol compounds," Zasloff, Shinnar, Kinney, Rao.

U.S. Pat. No. 5,840,936 (1998) for "Aminosterol compounds useful as inhibitors of the sodium/proton exchanger (NHE)," Zasloff, Shinnar, Rao, Kinney.

U.S. Pat. No. 5,847,172 (1998) for "Certain Aminosterol compounds and Pharmaceutical compositions including these compounds," Zasloff, Shinnar, Kinney, Jones.

U.S. Pat. No. 5,856,535 (1999) for "Aminosterol ester compounds," Zasloff, Kinney, Jones.

U.S. Pat. No. 5,874,597 (1999) for "Certain Aminosterol compounds and pharmaceutical compositions including these compounds," Jones, Issued Feb. 23, 1999.

U.S. Pat. No. 5,994,336 (1999) for "Method of inhibiting proliferation of cells by administering an aminosterol compound," Zasloff, Shinnar, Kinney, Rao, Issued Nov. 30, 1999.

U.S. Pat. No. 6,017,906 (2000) for "Polyamine conjugates for treatment of infection," Mintz, C S et al Intercardia, Inc., Issued Jan. 25, 2000

U.S. Pat. No. 6,143,738 (2000) for "Therapeutic uses for an aminosterol compound," Zasloff, Issued Nov. 7, 2000

U.S. Pat. No. 6,147,060 (2000) for "Treatment of carcinomas using squalamine in combination with other anticancer agents," Zasloff, Williams, Issued Nov. 14, 2000

U.S. Pat. No. 6,388,108 (2002) for "Aminosterol compounds and uses thereof," Rao, Feibush, Kinney, Zasloff, Noecker, Issued May 14, 2002.

U.S. Pat. No. 6,596,712 (2003) for "Treatment of carcinomas using squalamine in combination with other anticancer agents or modalities," Zasloff, Williams, Sokoloff, Issued Jul. 22, 2003.

U.S. Pat. No. 6,962,909 (2005) for "Treatment of neovascularization disorders with squalamine," Zasloff, Shinnar, Kinney, Jones, Issued Nov. 8, 2005.

Verdin et al., "Characterization of a common high-affinity receptor for reovirus serotypes 1 and 3 on endothelial cells," *J. Virol.*, 63(3): 1318-25 (1989).

White et al., "Therapeutic potential of vasoactive intestinal peptide and its receptors in neurological disorders," *CNS-Neurol. Disord. Drug Targets*, 9(5): 661-6 (2010).

Williams et al., "Squalamine treatment of human tumors in nu/nu mice enhances platinum-based chemotherapies," *Clin. Cancer Res.*, 7(3): 724-33 (2001).

WO 96/08270 (1996) for "Method for inhibiting sexually transmitted diseases using Magainin antimicrobials or Squalamine Compounds," Jacob, Zasloff, Williams, Bedi.

Yeung et al., "Membrane phosphatidylserine regulates surface charge and protein localization," *Science*, 319(5860): 210-3 (2008).

Yin et al., "Antiangiogenic treatment delays chondrocyte maturation and bone formation during limb skeletogenesis," *J. Bone Miner. Res.*, 17(1): 56-65 (2002).

Zasloff, M., "Antimicrobial peptides of multicellular organisms," *Nature*, 415(6870): 389-95 (2002).

Zasloff et al., "A spermine-coupled cholesterol metabolite from the shark with potent appetite suppressant and antidiabetic properties," *Int. J. Obes. Relat. Metab. Disord.*, 25(5): 689-97 (2001).

Zasloff et al., "Squalamine as a broad-spectrum systemic antiviral agent with therapeutic potential," *Proc. Natl. Acad. Sci. USA*, 108(38): 15978-83 (2011).

What is claimed:

1. A method of treating neurodegenerative processes associated with dementia of aging comprising orally administering to a subject in need thereof a composition comprising a pharmaceutically acceptable grade of at least one aminosterol, or a salt thereof, in an effective amount sufficient to produce a beneficial neuro-protective effect in the subject, wherein the aminosterol is squalamine or a pharmaceutically acceptable salt thereof, or Aminosterol 1436 or a pharmaceutically acceptable salt thereof; and
   wherein the effective amount is established by defining the initial dose required to induce the Aminosterol-Induced GI Response, which is the initial dose required to stimulate a change in bowel activity, nausea, secretory diarrhea, or any combination thereof.

2. The method of claim 1, wherein the Aminosterol-Induced GI Response produces one or more of the following in the subject:
   (a) improved bowel function;
   (b) improved fine motor skills;
   (c) improved articulation;
   (d) improved mood;
   (e) improved speech;
   (f) improved mood;
   (g) improved tremors;
   (h) improved coordination;
   (i) improved stamina;
   (j) improved balance;
   (k) improved cognitive function;
   (l) reduced dysphagia/improved swallowing;
   (m) improved autonomic function;
   (n) improved psychosis; and/or
   (o) improved daytime wakefulness.

3. The method of claim 1, wherein the aminosterol composition is co-administered or combined with one or more drugs commonly prescribed to treat degenerative processes associated with dementia of aging.

4. The method of claim 3, wherein the one or more drugs commonly prescribed to treat neurodegenerative processes associated with dementia of aging are selected from the group consisting of levodopa, a dopa decarboxylase inhibitor, a COMT inhibitor, dopamine agonists, MAO-B inhibitors, carbidopa, benserazide, tolcapone, entacapone, bromocriptine, pergolide, pramipexole, ropinirole, piribedil, cabergoline, apomorphine, lisuride, rotigotine, selegiline, rasagiline, amantadine, anticholinergics, clozapine, cholinesterase inhibitors, and modafinil.

5. The method of claim 3, wherein the one or more drugs commonly prescribed to treat neurodegenerative processes associated with dementia of aging are selected from the group consisting of Glutamate, Antipsychotic drugs, Huperzine A, acetylcholinesterase inhibitors, NMDA receptor antagonists, memantine, donepezil, galantamine, and rivastigmine.

6. The method of claim 3, wherein the one or more drugs commonly prescribed to treat neurodegenerative processes associated with dementia of aging are selected from the group consisting of antipsychotic drugs, drugs used to treat dystonia, GABA-regulating drugs, dopamine-regulators, anticonvulsants, drugs used to treat depression, amantadine, tetrabenazine, Dopamine blockers, and co-enzyme Q10.

7. The method of claim 3, wherein the one or more drugs commonly prescribed to treat neurodegenerative processes associated with dementia of aging are selected from the group consisting of corticosteroids, methylprednisolone, plasmapheresis, fingolimod, interferon beta-1a, interferon beta-1b, glatiramer acetate, mitoxantrone, natalizumab, alemtuzumab, daclizumab, rituximab, dirucotide, BHT-3009, cladribine, dimethyl fumarate, estriol, fingolimod, laquinimod, minocycline, statins, temsirolimus teriflunomide, and naltrexone.

8. The method of claim 1, wherein the Aminosterol-Induced GI Response results in:
   (a) triggering the production of neuro-protective hormones or neuropeptides which function to treat neurodegenerative processes associated with dementia of aging; and/or
   (b) prevent the accumulation of alpha synuclein, thereby treating neurodegenerative processes associated with dementia of aging.

9. The method of claim 1, wherein the aminosterol or the pharmaceutically acceptable salt thereof is:
   (a) isolated from *Squalus acanthias*.

10. The method of claim 1, wherein the Aminosterol-Induced GI Response:
    (a) triggers the production of neuro-protective hormones or neuropeptides in the brain, which function to prevent onset or development of degenerative processes associated with dementia of aging; and/or
    (b) physically reduces the concentration of membrane bound beta-amyloid from its target membranes, which functions to prevent onset or development of degenerative processes associated with dementia of aging.

11. The method of claim 1, comprising administering to the subject in need a combination of:
    (a) a pharmaceutically acceptable grade of squalamine or a pharmaceutically acceptable salt thereof; and
    (b) a pharmaceutically acceptable grade of Aminosterol 1436 or a pharmaceutically acceptable salt thereof,
    wherein the squalamine or a pharmaceutically acceptable salt thereof and the Aminosterol 1436 or a pharmaceutically acceptable salt thereof are present in the same or separate compositions.

\* \* \* \* \*